(12) United States Patent
Weidanz et al.

(10) Patent No.: US 9,555,108 B2
(45) Date of Patent: Jan. 31, 2017

(54) TCR MIMIC ANTIBODIES AS VASCULAR TARGETING TOOLS

(75) Inventors: John A. Weidanz, Abilene, TX (US); Ulrich Bickel, Amarillo, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 14/007,164

(22) PCT Filed: Mar. 23, 2012

(86) PCT No.: PCT/US2012/030406
§ 371 (c)(1),
(2), (4) Date: Jan. 30, 2014

(87) PCT Pub. No.: WO2012/129520
PCT Pub. Date: Sep. 27, 2014

(65) Prior Publication Data
US 2014/0134191 A1    May 15, 2014

Related U.S. Application Data

(60) Provisional application No. 61/467,215, filed on Mar. 24, 2011.

(51) Int. Cl.
| | | |
|---|---|---|
| A61K 38/00 | (2006.01) | |
| A61K 39/395 | (2006.01) | |
| A61K 47/48 | (2006.01) | |
| C07K 16/18 | (2006.01) | |
| C07K 16/28 | (2006.01) | |
| A61K 39/00 | (2006.01) | |

(52) U.S. Cl.
CPC ..... *A61K 39/3955* (2013.01); *A61K 47/48561* (2013.01); *C07K 16/18* (2013.01); *C07K 16/28* (2013.01); *C07K 16/2833* (2013.01); *A61K 2039/505* (2013.01); *C07K 2317/32* (2013.01); *C07K 2317/77* (2013.01); *C07K 2317/94* (2013.01)

(58) Field of Classification Search
CPC ...... A61K 61/45; A61K 31/57; A61K 31/165; C07K 14/47
See application file for complete search history.

(56) References Cited

U.S. PATENT DOCUMENTS

| | | | |
|---|---|---|---|
| 4,816,567 A | 3/1989 | Cabilly et al. | |
| 5,225,539 A | 7/1993 | Winter | |
| 5,545,806 A | 8/1996 | Kay et al. | |
| 5,545,807 A | 8/1996 | Bruggeman et al. | |
| 5,569,825 A | 10/1996 | Kay et al. | |
| 5,625,126 A | 4/1997 | Kay et al. | |
| 5,633,425 A | 5/1997 | Kay et al. | |
| 5,661,016 A | 8/1997 | Kay et al. | |
| 5,712,120 A | 1/1998 | Mateo de Acosta del Rio et al. | |
| 5,861,155 A | 1/1999 | Lin | |
| 5,869,619 A | 2/1999 | Studnicka | |
| 5,916,771 A | 6/1999 | Davis et al. | |
| 5,939,598 A | 8/1999 | Jakobovits et al. | |
| 6,054,927 A | 4/2000 | Brickell | |
| 6,180,370 B1 | 1/2001 | Queen et al. | |
| 7,147,839 B2 * | 12/2006 | Sampath et al. | 424/9.2 |
| 2002/0150914 A1 | 10/2002 | Andersen et al. | |
| 2003/0223994 A1 | 12/2003 | Hoogenboom et al. | |
| 2004/0191260 A1 | 9/2004 | Cohen et al. | |
| 2006/0034850 A1 * | 2/2006 | Weidanz et al. | 424/155.1 |
| 2007/0092530 A1 | 4/2007 | Weidanz et al. | |
| 2009/0304679 A1 | 12/2009 | Weidanz | |
| 2010/0196266 A1 | 8/2010 | Goldenberg | |

FOREIGN PATENT DOCUMENTS

| | | |
|---|---|---|
| WO | 94/02602 | 2/1994 |
| WO | 96/33735 A1 | 10/1996 |
| WO | 96/34096 A1 | 10/1996 |
| WO | 03068201 A2 | 2/2003 |
| WO | 03/068201 A2 | 8/2003 |

OTHER PUBLICATIONS

Banks et. al. Characteristics of compounds that cross the blood-brain barrier teaches that the blood-brain barrier, BMC Neurology 2009, 9 Suppl. 1:S3.*
Yoram. Peptide-specific killing of antigen-presenting cells by a recombinant antibody-toxin fusion protein targeted to major histocompatibility complex peptide class I complexes with T cell receptor-like specificity, Proc. Natl. Acad. Sci. USA, Immunology, vol. 94, pp. 4631-4636, Apr. 1997.*
Verma. TCR Mimic Monoclonal Antibody Targets a Specific Peptide/HLA Class I Complex and Significantly Impedes Tumor Growth In Vivo Using Breast Cancer Models, The Journal of Immunology, 2010, 184: 2156-2165.*
Bhattacharya et. al. A novel vascular targeting strategy for brain-derived endothelial cells using a TCR mimic antibody, J Cell Physiol. Nov. 2010; 225(3): 664-672.*
Wolburg et. al., J Cell Sci. May 1994, 107 ( Pt 5):1347-57.*
Svetlana et. al. Current Neuropharmacology, 2008, 6, 179-192.*
Weidanz, Int. Rev. Immunol. 2011; 30(5-6): 328-340.*

(Continued)

*Primary Examiner* — Jeanette Lieb
(74) *Attorney, Agent, or Firm* — Edwin S. Flores; Chainey P. Singleton; Chalker Flores, LLP

(57) ABSTRACT

The present invention includes a method of delivering a therapeutic agent into and across an endothelial cell (EC) in a subject in need thereof, comprising: attaching to a T Cell receptor mimic (TCR mimic) an active agent to form a therapeutic agent; and administering to the subject the therapeutic agent in a pharmaceutically acceptable carrier, wherein the therapeutic agent effectively crosses the EC microvascular barrier. Furthermore, the present invention relates to methods of treating diseases (particularly neuronal diseases) or conditions comprising identifying a subject in need of such a treatment and administering to said subject a composition comprising a TCR mimic conjugated to an active agent.

21 Claims, 11 Drawing Sheets

(56) References Cited

OTHER PUBLICATIONS

Verma, J. Immunol 2010; 184:2156-2165; Prepublished online 11.*
Bhattacharya, R et al (2010). A novel vascular targeting strategy for brain-derived endothelial cells using a TCR mimic antibody. Journal of Cellular Physiology 225: 664-672.
International Search Report (AU) PCT/US2012/030406 dated May 28, 2012.
Bhattacharya, R et al., "A novel vascular targeting strategy for brain-derived endothelial cells using a TCR mimic antibody" J Cell Physio, 2010; 225: 664-672.
Lee, H J et al., "Targeting rat anti-mouse transferrin receptor monoclonal antibodies through blood-brain barrier in mouse" J Pharmacol ExpTher 2000;292: 1048-1052.
Neethling, F A et al., "Assessing vaccine potency using TCR mimic antibodies" Vaccine 2008; 26: 3092-3102.
Verma, B et al., "Direct discovery and validation of a peptide/MHC epitope expressed in primary human breast cancer cells using a TCRm monoclonal antibody with profound antitumor properties" Cancer Immunollmmunother 201 0; 59: 563-573.
Verma, B et al., "TCR mimic monoclonal antibody targets as pecific peptide/HLA class Ic omplex and significantly impedes tumor growth in vivo using breast cancer models" J Immuno, 2010; 184: 2156-2165.
Weidanz, J A et al., "Levels of specific peptide-HLA class I complex predicts tumor cell susceptibility to CTL killing" J Immuno/2006; 177: 5088-5097.
Weidanz, JA et al., "Development and implementation of a direct detection, quantitation and validation system for class IM HCs elf-peptide epitopes" J Immunol Methods 2007; 318: 47-58.
Weksler, B B et al., "Blood-brain barrier-specific properties of a human adult brain endothelial cell line" Faseb J, 2005; 19: 1872-1874.
Chothia, Cyrus et al., "Conformations of immunoglobulin hypervariable regions" Nature Dec. 28, 1989 342: 877-883.
Novotny, Jiri et al., "Structural invariants of antigen binding: Comparison of immunoglobulin VL-VH and VL-VL domain dimers" Proc. Natl. Acad. Sci. Jul. 1985 82: 4592-4596.

* cited by examiner

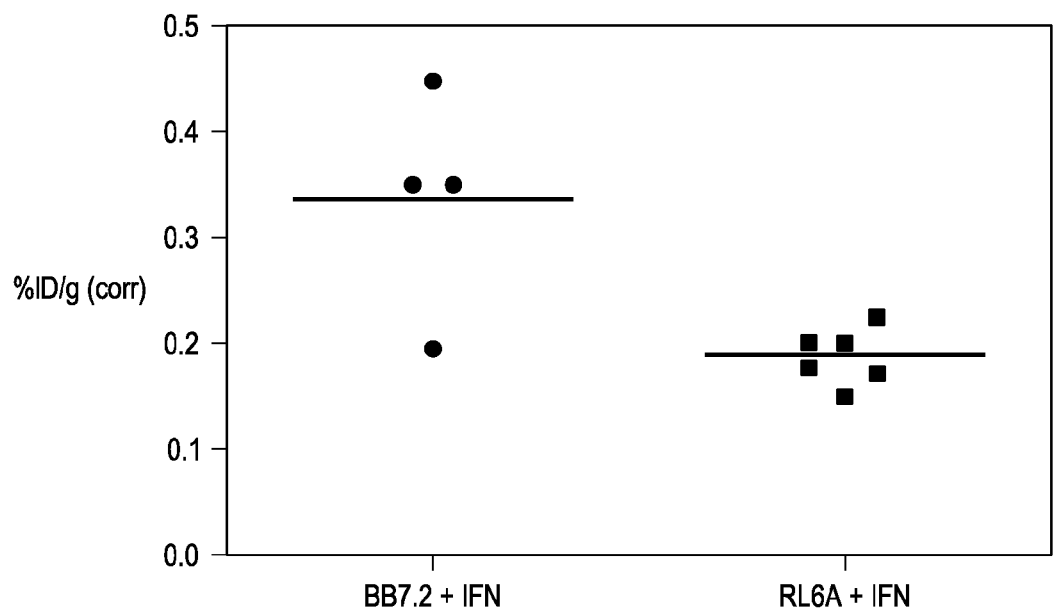
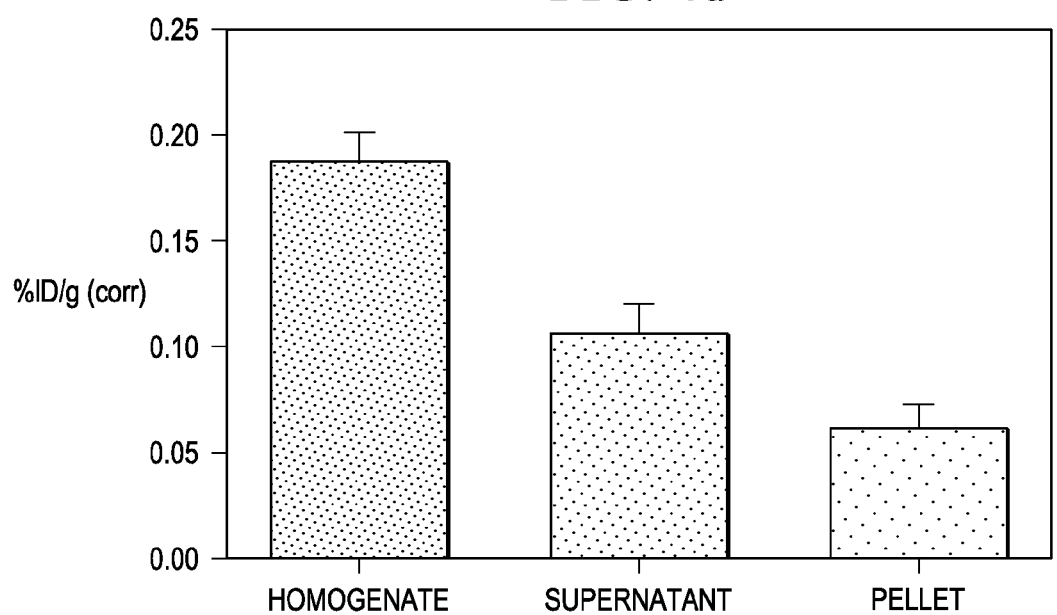

TCR MIMIC ANTIBODIES AS VASCULAR TARGETING TOOLS

CROSS-REFERENCE TO RELATED APPLICATIONS

This application claims priority to, and is the National Stage of International Application No. PCT/US2012/030406 filed on Mar. 23, 2012 and claims the priority of U.S. Provisional Patent Application Ser. No. 61/467,215, filed on Mar. 24, 2011, the contents of which are incorporated by reference herein in their entirety.

TECHNICAL FIELD OF THE INVENTION

The present invention relates in general to the field of cell targeting, and more particularly, to T cell receptor mimics that target peptide-MHC complexes.

BACKGROUND OF THE INVENTION

Without limiting the scope of the invention, its background is described in connection with T Cell Receptor mimics.

The present inventors have previously demonstrated Antibodies as T cell receptor mimics, methods of production and uses for the same. For example, United States Patent Application No. 20090304679, filed by Weidanz teaches a methodology of producing and utilizing antibodies that recognize peptides associated with a tumorigenic or disease state, wherein the peptides are displayed in the context of HLA molecules. These antibodies may be utilized in therapeutic methods of mediating cell lysis.

The inventors have previously taught that Class I major histocompatibility complex (MHC) molecules, designated HLA class I in humans, bind and display peptide antigen ligands upon the cell surface. The peptide antigen ligands presented by the class I MHC molecule are derived from either normal endogenous proteins ("self") or foreign proteins ("non-self") introduced into the cell. Non-self proteins may be products of malignant transformation or intracellular pathogens such as viruses. In this manner, class I MHC molecules convey information regarding the internal milieu of a cell to immune effector cells including but not limited to, CD8.sup.+ cytotoxic T lymphocytes (CTLs), which are activated upon interaction with "non-self" peptides, thereby lysing or killing the cell presenting such "non-self" peptides.

Class II MHC molecules, designated HLA class II in humans, also bind and display peptide antigen ligands upon the cell surface. Unlike class I MHC molecules which are expressed on virtually all nucleated cells, class II MHC molecules are normally confined to specialized cells, such as B lymphocytes, macrophages, dendritic cells, and other antigen presenting cells which take up foreign antigens from the extracellular fluid via an endocytic pathway. The peptides they bind and present are derived from extracellular foreign antigens, such as products of bacteria that multiply outside of cells, wherein such products include protein toxins secreted by the bacteria that often have deleterious and even lethal effects on the host (e.g., human). In this manner, class II molecules convey information regarding the fitness of the extracellular space in the vicinity of the cell displaying the class II molecule to immune effector cells, including but not limited to, CD4+ helper T cells, thereby helping to eliminate such pathogens. The extermination of such pathogens is accomplished by both helping B cells make antibodies against microbes, as well as toxins produced by such microbes, and by activating macrophages to destroy ingested microbes.

Class I and class II HLA molecules exhibit extensive polymorphism generated by systematic recombinatorial and point mutation events during cell differentiation and maturation resulting from allelic diversity of the parents; as such, hundreds of different HLA types exist throughout the world's population, resulting in a large immunological diversity. Such extensive HLA diversity throughout the population is the root cause of tissue or organ transplant rejection between individuals as well as of differing individual susceptibility and/or resistance to infectious diseases. HLA molecules also contribute significantly to autoimmunity and cancer.

Class I MHC molecules alert the immune response to disorders within host cells. Peptides which are derived from viral- and tumor-specific proteins within the cell are loaded into the class I molecule's antigen binding groove in the endoplasmic reticulum of the cell and subsequently carried to the cell surface. Once the class I MHC molecule and its loaded peptide ligand are on the cell surface, the class I molecule and its peptide ligand are accessible to cytotoxic T lymphocytes (CTL). CTLs survey the peptides presented by the class I molecule and destroy those cells harboring ligands derived from infectious or neoplastic agents within that cell.

The value of monoclonal antibodies which recognize peptide-MHC complexes has been recognized by others (see for example Reiter, US Publication No. US 2004/0191260 A1, filed Mar. 26, 2003; Andersen et al., US Publication No. US 2002/0150914 A1, filed Sep. 19, 2001; Hoogenboom et al., US Publication No. US 2003/0223994 A1, filed Feb. 20, 2003; and Reiter et al., PCT Publication No. WO 03/068201 A2, filed Feb. 11, 2003). However, these processes employ the use of phage display libraries that do not produce a whole, ready-to-use antibody product. The majority of these antibodies were isolated from bacteriophage libraries as Fab fragments (Cohen et al., 2003; Held et al., 2004; and Chames et al., 2000) and have not been examined for anti-tumor activity since they do not activate innate immune mechanisms (e.g., complement-dependent cytotoxicity [CDC]) or antibody-dependent cellular cytotoxicity (ADCC). Demonstration of anti-tumor activity is critical, as therapeutic mAbs are thought to act through several mechanisms, which engage the innate response, including antibody or complement-mediated phagocytosis by macrophage, CDC and ADCC (Liu et al., 2004; Prang et al., 2005; Akewanlop et al., 2001; Clynes et al., 2000; and Masui et al., 1986). These prior art methods also have not demonstrated production of antibodies capable of staining tumor cells in a robust manner, implying that they are of low affinity or specificity. The immunogen employed in the prior art methods uses MHC which has been "enriched" for one particular peptide, and therefore such immunogen contains a pool of peptide-MHC complexes and is not loaded solely with the peptide of interest. In addition, there has not been a concerted effort in these prior art methods to maintain the structure of the three dimensional epitope formed by the peptide/HLA complex, which is essential for generation of the appropriate antibody response. For these reasons, immunization protocols presented in these prior art references had to be carried out over long periods of time (i.e., approximately 5 months or longer).

In addition, the vast majority of phage-derived antibodies produced by the prior art methods will not fold right in mammalian cells due to their selection for expression in prokaryotic or simple eukaryotic systems; generally, <1% of phage-derived antibodies will efficiently fold in mammalian cells, thus greatly increasing the number of candidates that must be screened and virtually assuring that interesting lead candidates with the most desirable binding properties are non-producible in mammalian cells due to the infrequency of success. Supporting this contention is the fact that very few phage-derived antibodies have proceeded into clinical investigation, and no phage-derived antibody has been approved for use as a therapeutic. All approved therapeutic antibodies have their discovery origin from a mammalian species.

Thus, the prior art phage-derived antibodies are not useful for making anti-MHC/peptide complexes, as they typically exhibit low affinity, low robustness, low capability to grow and fold, and as they are generally laborious to implement and have not been shown to be viable for approved therapeutic use.

SUMMARY OF THE INVENTION

The present inventors recognized that a need exists in the art for therapeutic antibodies with novel recognition specificity for peptide-HLA domain in complexes present on the surface of epithelial cells throughout the body. The presently claimed and disclosed invention provides innovative processes for using antibody molecules endowed with unique antigen recognition specificities for peptide-HLA complexes, as peptide-HLA molecules, to not only enter endothelial cells at the blood-brain-barrier (BBB), but trancytose past the BBB into protected neural tissues.

In one embodiment, the present invention includes a method of delivering a therapeutic agent into and across an endothelial cell (EC) in a subject in need thereof, comprising: attaching to a TCR mimic an active agent to form a therapeutic agent; and administering to the subject the therapeutic agent in a pharmaceutically acceptable carrier, wherein the therapeutic agent effectively crosses the EC microvascular barrier. In one aspect, the barrier being crossed is the blood-brain barrier (BBB), blood-retina barrier, blood-nerve barrier or blood-spinal cord barrier in a subject with (i) a CNS disease or disorder or (ii) a peripheral disease or disorder with CNS involvement. In another aspect, the disease or disorder is: a neurodegenerative disorder; a neuropsychiatric disorder; a central nervous system (CNS) disorder selected from the group consisting of a brain tumor, epilepsy, migraine, narcolepsy, insomnia, chronic fatigue syndrome, mountain sickness, encephalitis, meningitis, and AIDS-related dementia. In another aspect, the therapeutic agent or carrier is directly conjugated to a targeting molecule by: (a) non-specific or specific protein-protein interaction; (b) covalent bonding; (c) non-covalent bonding; or (d) coordinating chemical bonding; which conjugation is optionally effected via a spacer or linker that bridges between the therapeutic agent or carrier and the targeting molecule. In another aspect, the therapeutic agent-targeting molecule conjugate or carrier-targeting molecule conjugate is a recombinant fusion or hybrid polypeptide. In another aspect, the step of administering is (a) by continuous intravenous or intraarterial infusion; or (b) by bolus injection by an intravenous, intramuscular, intraarterial, or intralesional route. In another aspect, the active agent is an antineoplastic agent, a cytotoxic agent, anti-inflammatory, a hormone, an enzyme, a neurotransmitter, a neurotrophic factor, antibiotics, a cytokine, or a neuropeptide. In another aspect, the subject has or is suspected of having neuronal cell death associated with Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, or anoxia due to surgery.

Yet another embodiment of the present invention includes a method of delivering a therapeutic agent into and across a microvascular blood-central nervous system (CNS) barrier in a subject, comprising: administering to a subject with at least one of a CNS disease or disorder or a peripheral disease or disorder with CNS involvement, a composition comprising: a TCR mimic an active agent that together form a therapeutic agent; and a pharmaceutically acceptable carrier, wherein the therapeutic agent is encapsulated in a nanocontainer to which is linked the targeting molecule, wherein an effective barrier-entering and barrier crossing amount of the therapeutic agent enters and crosses the microvascular blood CNS barrier.

In one aspect, the disease or disorder is: a neurodegenerative disorder; a neuropsychiatric disorder; a central nervous system (CNS) disorder selected from the group consisting of a brain tumor, epilepsy, migraine, narcolepsy, insomnia, chronic fatigue syndrome, mountain sickness, encephalitis, meningitis, and AIDS-related dementia. In another aspect, the therapeutic agent or carrier is directly conjugated to a targeting molecule by: (a) non-specific or specific protein-protein interaction; (b) covalent bonding; (c) non-covalent bonding; or (d) coordinating chemical bonding; which conjugation is optionally effected via a spacer or linker that bridges between the therapeutic agent or carrier and the targeting molecule. In another aspect, the therapeutic agent-targeting molecule conjugate or carrier-targeting molecule conjugate is a recombinant fusion or hybrid polypeptide. In another aspect, the step of administering is (a) by continuous intravenous or intraarterial infusion; or (b) by bolus injection by an intravenous, intramuscular, intraarterial, or intralesional route. In another aspect, the subject has or is suspected of having neuronal cell death associated with Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, or anoxia due to surgery. In another aspect, the active agent is an antineoplastic agent, a cytotoxic agent, anti-inflammatory, a hormone, an enzyme, a neurotransmitter, a neurotrophic factor, antibiotics, a cytokine, or a neuropeptide.

Yet another embodiment of the present invention includes a method for treating a neuronal disease or condition comprising: identifying a subject in need of such treatment for the neuronal disease or condition; administering to the subject in need of such treatment a neuroprotective and/or neurorestorative agent in an amount effective to treat the disorder in the subject, wherein the agent comprises: a TCR mimic that targets an MHC-peptide combination found on the surface of an endothelial cells of the neuronal vasculature that is conjugated to an active agent to form a therapeutic agent. In one aspect, the disease or disorder is: a neurodegenerative disorder; a neuropsychiatric disorder; a central nervous system (CNS) disorder selected from the group consisting of a brain tumor, epilepsy, migraine, narcolepsy, insomnia, chronic fatigue syndrome, mountain sickness, encephalitis, meningitis, and AIDS-related dementia. In another aspect, the therapeutic agent or carrier is directly conjugated to a targeting molecule by: (a) non-specific or specific protein-protein interaction; (b) covalent bonding; (c) non-covalent bonding; or (d) coordinating chemical bonding; which conjugation is optionally effected via a spacer or linker that bridges between the therapeutic agent or carrier and the targeting molecule. In another aspect, the therapeutic agent-targeting molecule conjugate or carrier-targeting molecule conjugate is a recombinant fusion or hybrid polypeptide. In another aspect, the step of administering is at least one of (a) by continuous intravenous or intraarterial infusion; or (b) by bolus injection by an intravenous, intramuscular, intraarterial, or intralesional route. In another aspect, the subject has or is suspected of having neuronal cell death associated with Parkinson's disease (PD), Alzheimer's disease, Lewy body disease, stroke, brain injury, spinal cord injury, aging, cardiovascular disease, macular degeneration, toxin exposure, poisoning, Tardive dyskinesia, high altitude sickness, CNS diseases with neuronal degeneration, metabolic disorder, infection, anoxia, or anoxia due to surgery. In another aspect, the active agent is an antineoplastic agent, a cytotoxic agent, anti-inflammatory, a hormone, an enzyme, a neurotransmitter, a neurotrophic factor, antibiotics, a cytokine, or a neuropeptide.

Yet another embodiment of the present invention includes a method for treating a disease or condition in which a therapeutic agent has to cross an epithelial layer of a vasculature comprising: identifying a subject in need of such treatment for the disease or condition; administering to the subject in need of such treatment the therapeutic agent in an amount effective to treat the disorder in the subject, wherein the agent comprises: a TCR mimic that targets an MHC-peptide combination found on the surface of an endothelial cells that is conjugated to an active agent to form a therapeutic agent. In one aspect, the active agent is an antineoplastic agent, a cytotoxic agent, anti-inflammatory, a hormone, an enzyme, a neurotransmitter, a neurotrophic factor, antibiotics, a cytokine, or a neuropeptide.

BRIEF DESCRIPTION OF THE DRAWINGS

For a more complete understanding of the features and advantages of the present invention, reference is now made to the detailed description of the invention along with the accompanying figures and in which:

(FIG. 1c) and (FIG. 1d) show the effect of mild acid wash on binding to hCMEC/D3 cells. Competition by 100-fold molar excess of unlabeled antibody is indicated as "+cold" or "+comp".

FIGS. 4a-4d. Brain uptake in transgenic mouse strain 3475. (FIG. 4a) shows Vd brain, which is the apparent volume of distribution at 60 min (=ratio of concentrations in brain and plasma) after injection of 30 µg/kg tracer. Absence or presence of IFNγ pretreatment in these animals over 48 h is indicated as +IFN or -IFN. No effect of IFNγ on Vd of UPC10 was seen and both UPC10 groups were pooled to get an estimate of brain plasma volume (8.5±1.4 UL/g, mean±SD, n=6).

FIG. 5c shows the brain concentrations calculated from (FIG. 5a) after correction for brain plasma volume (8.5 µl/g).

DETAILED DESCRIPTION OF THE INVENTION

Figure 1A:
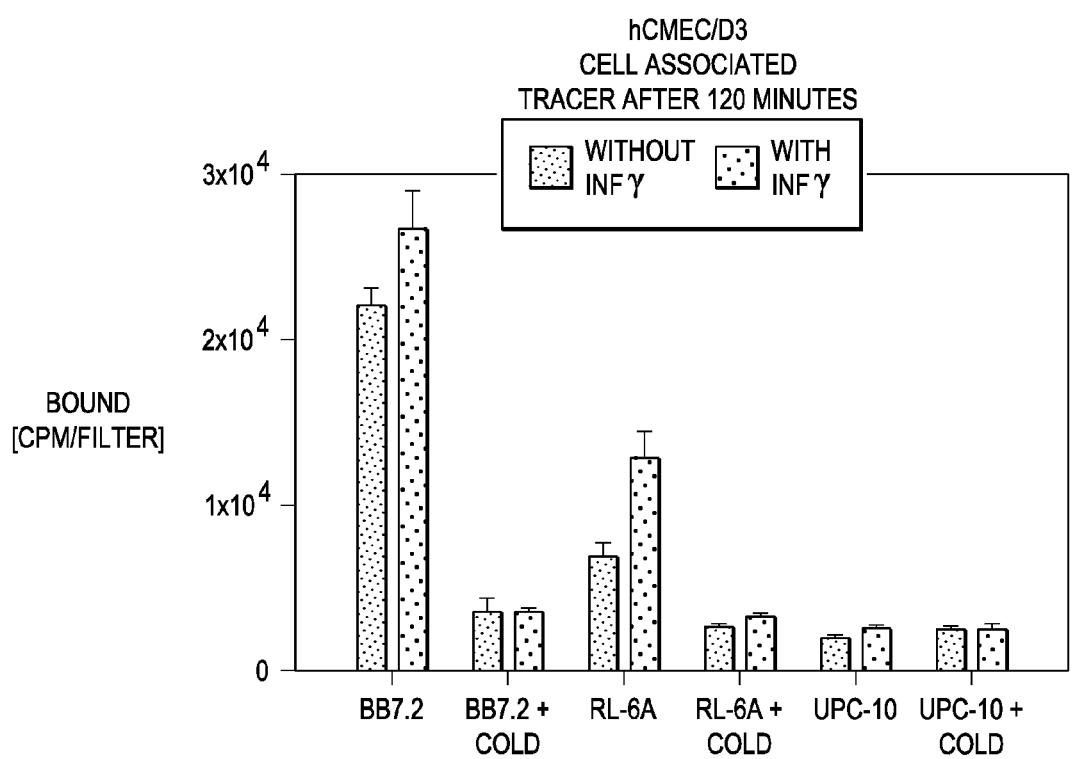
FIGS. 1a-1d. Binding of $^{125}$I-labeled antibodies to hCMEC/D3 monolayers (FIG. 1a) or HH8 monolayers (FIG. 1b). Tracer concentrations were 2 nM.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the terms "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counterreceptor by at least about 20%, 40%, 60% or 80%, and more usually greater than about 85% (as measured in an in vitro competitive binding assay).

As used herein, the term "MHC" refers to the Major Histocompatibility Complex, which is defined as a set of gene loci specifying major histocompatibility antigens. The term "HLA" as used herein will be understood to refer to Human Leukocyte Antigens, which is defined as the histocompatibility antigens found in humans. As used herein, "HLA" is the human form of "MHC".

As used herein, the terms "MHC light chain" and "MHC heavy chain" refer to portions of the MHC molecule. Structurally, class I molecules are heterodimers comprised of two noncovalently bound polypeptide chains, a larger "heavy" chain (a) and a smaller "light" chain ($\beta_2$-microglobulin or $\beta_2$m). The polymorphic, polygenic heavy chain (45 kDa), encoded within the MHC on chromosome six, is subdivided into three extracellular domains (designated 1, 2, and 3), one intracellular domain, and one transmembrane domain. The two outermost extracellular domains, 1 and 2, together form the groove that binds antigenic peptide. Thus, interaction with the TCR occurs at this region of the protein. The 3 domain of the molecule contains the recognition site for the CD8 protein on the CTL; this interaction serves to stabilize the contact between the T cell and the APC. The invariant light chain (12 kDa), encoded outside the MHC on chromosome 15, consists of a single, extracellular polypeptide. The terms "MHC light chain", "β-2-microglobulin", and "β$_2$m" may be used interchangeably herein.

As used herein, the term "epitope" refers to any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is to specifically bind an antigen when the dissociation constant is <1 µM, or <100 nM, or <10 nM.

As used herein, the term "antibody" is used in the broadest sense, and specifically covers monoclonal antibodies (including full length monoclonal antibodies), polyclonal antibodies, multispecific antibodies (e.g., bispecific antibodies), and antibody fragments (e.g., Fab, F(ab')$_2$ and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond. While the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82 4592-4596 (1985), relevant portions incorporated herein by reference.

As used herein, an "isolated" antibody is one that has been identified and separated and/or recovered from a component of the environment in which it was produced. Contaminant components of its production environment are materials, which would interfere with diagnostic or therapeutic uses for the antibody, and may include enzymes, hormones, and other proteinaceous or nonproteinaceous solutes. In certain embodiments, the antibody will be purified as measurable by at least three different methods: 1) to greater than 50% by weight of antibody as determined by the Lowry method, such as more than 75% by weight, or more than 85% by weight, or more than 95% by weight, or more than 99% by weight; 2) to a degree sufficient to obtain at least 10 residues of N-terminal or internal amino acid sequence by use of a spinning cup sequentator, such as at least 15 residues of sequence; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "antibody mutant" refers to an amino acid sequence variant of an antibody wherein one or more of the amino acid residues have been modified. Such mutants necessarily have less than 100% sequence identity or similarity with the amino acid sequence having at least 75% amino acid sequence identity or similarity with the amino acid sequence of either the heavy or light chain variable domain of the antibody, such as at least 80%, or at least 85%, or at least 90%, or at least 95%.

As used herein, the term "variable" in the context of variable domain of antibodies, refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains. There are at least two techniques for determining CDRs: (1) an approach based on cross-species sequence variability (i.e., Kabat et al., Sequences of Proteins of Immunological Interest (National Institute of Health, Bethesda, Md. 1987); and (2) an approach based on crystallographic studies of antigen-antibody complexes (Chothia, C. et al. (1989), Nature 342: 877). The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al.) The constant domains are not involved directly in binding an antibody to an antigen, but exhibit various effector function, such as participation of the antibody in antibody-dependent cellular toxicity.

As used herein, the term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). As used herein, "functional fragment" with respect to antibodies, refers to Fv, F(ab) and F(ab')$_2$ fragments.

As used herein, the "Fv" fragment is the minimum antibody fragment which contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment [also designated as F(ab)] also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

The light chains of antibodies (immunoglobulin) from any vertebrate species can be assigned to one of two clearly distinct types, called kappa (κ) and lambda (λ), based on the amino sequences of their constant domain.

Depending on the amino acid sequences of the constant domain of their heavy chains, "immunoglobulins" can be assigned to different classes. There are at least five (5) major classes of immunoglobulins: IgA, IgD, IgE, IgG and IgM, and several of these may be further divided into subclasses (isotypes), e.g., IgG-1, IgG-2, IgG-3 and IgG4; IgA-1 and IgA-2. The heavy chains constant domains that correspond to the different classes of immunoglobulins are called α, δ, ε, γ, and μ, respectively. The subunit structures and three-dimensional configurations of different classes of immunoglobulins are well known.

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed and claimed invention may be made by the hybridoma method first described by Kohler and Milstein, Nature 256, 495 (1975), relevant portions incorporated herein by reference.

All monoclonal antibodies utilized in accordance with the presently disclosed and claimed invention will be either (1) the result of a deliberate immunization protocol, as described in more detail herein below; or (2) the result of an immune response that results in the production of antibodies naturally in the course of a disease or cancer. These monoclonal antibodies are distinguished from the prior art antibodies which are phage-derived, because the prior art phage-derived antibodies are not useful for making anti-MHC/peptide complexes, as they typically exhibit low affinity, low robustness, low capability to grow and fold, and as they are generally laborious to implement and have not been shown to be viable for approved therapeutic use.

The uses of the monoclonal antibodies of the presently disclosed and claimed invention may require administration of such or similar monoclonal antibody to a subject, such as a human. However, when the monoclonal antibodies are produced in a non-human animal, such as a rodent, administration of such antibodies to a human patient will normally elicit an immune response, wherein the immune response is directed towards the antibodies themselves. Such reactions limit the duration and effectiveness of such a therapy. In order to overcome such problem, the monoclonal antibodies of the presently disclosed and claimed invention can be "humanized", that is, the antibodies are engineered such that antigenic portions thereof are removed and like portions of a human antibody are substituted therefore, while the antibodies' affinity for specific peptide/MHC complexes is retained. This engineering may only involve a few amino acids, or may include entire framework regions of the antibody, leaving only the complementarity determining regions of the antibody intact. Several methods of humanizing antibodies are known in the art and are disclosed in U.S. Pat. No. 6,180,370, issued to Queen et al on Jan. 30, 2001; U.S. Pat. No. 6,054,927, issued to Brickell on Apr. 25, 2000; U.S. Pat. No. 5,869,619, issued to Studnicka on Feb. 9, 1999; U.S. Pat. No. 5,861,155, issued to Lin on Jan. 19, 1999; U.S. Pat. No. 5,712,120, issued to Rodriquez et al on Jan. 27, 1998; and U.S. Pat. No. 4,816,567, issued to Cabilly et al on Mar. 28, 1989, relevant portions incorporated herein by reference.

Humanized forms of antibodies are chimeric immunoglobulins, immunoglobulin chains or fragments thereof (such as Fv, Fab, Fab', F(ab')2 or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., 1986; Riechmann et al., 1988; Verhoeyen et al., 1988), by substituting rodent CDRs or CDR sequences for the corresponding sequences of a human antibody. (See also U.S. Pat. No. 5,225,539.) In some instances, $F_v$ framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, 1992).

The presently disclosed and claimed invention further includes the use of fully human monoclonal antibodies against specific peptide/MHC complexes. Fully human antibodies essentially relate to antibody molecules in which the entire sequence of both the light chain and the heavy chain, including the CDRs, arise from human genes. Such antibodies are termed "human antibodies" or "fully human antibodies" herein. Human monoclonal antibodies can be prepared by the trioma technique; the human B-cell hybridoma technique (see Kozbor, et al., Hybridoma, 2:7

(1983)) and the EBV hybridoma technique to produce human monoclonal antibodies (see Cole, et al., PNAS 82:859 (1985)). Human monoclonal antibodies may be utilized in the practice of the presently disclosed and claimed invention and may be produced by using human hybridomas (see Cote, et al., PNAS 80:2026 (1983)) or by transforming human B-cells with Epstein Barr Virus in vitro (see Cole, et al., 1985), relevant portions incorporated herein by reference.

In addition, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example but not by way of limitation, in U.S. Pat. Nos. 5,545,807; 5,545,806; 5,569,825; 5,625,126; 5,633,425; 5,661,016, and in Marks et al., J Biol. Chem. 267:16007, (1992); Lonberg et al., Nature, 368:856 (1994); Morrison, 1994; Fishwild et al., Nature Biotechnol. 14:845 (1996); Neuberger, Nat. Biotechnol. 14:826 (1996); and Lonberg and Huszar, Int Rev Immunol. 13:65 (1995), relevant portions incorporated herein by reference.

Human antibodies may additionally be produced using transgenic nonhuman animals which are modified so as to produce fully human antibodies rather than the animal's endogenous antibodies in response to challenge by an antigen. (See PCT publication WO 94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. One embodiment of such a nonhuman animal is a mouse, and is termed the XENOMOUSE™ as disclosed in PCT Publication Nos. WO 96/33735 and WO 96/34096. This animal produces B cells that secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598, issued to Kucherlapati et al. on Aug. 17, 1999, and incorporated herein by reference. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771, issued to Hori et al. on Jun. 29, 1999, and incorporated herein by reference. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

As used herein, the term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)), incorporated herein by reference).

The term patient includes human and veterinary subjects.

As used herein, a "liposome" is a small vesicle composed of various types of lipids, phospholipids and/or surfactant. The components of the liposome are commonly arranged in a bilayer formation, similar to the lipid arrangement of biological membranes.

As used herein, the term "Treatment" refers to both therapeutic treatment and prophylactic or preventative measures. Those in need of treatment include those already with the disorder as well as those in which the disorder is to be prevented.

As used herein, the term "disorder" refers to any condition that would benefit from treatment with the polypeptide. This includes chronic and acute disorders or diseases including those infectious or pathological conditions that predispose the mammal to the disorder in question.

As mentioned hereinabove, depending on the application and purpose, the T cell receptor mimic of the presently disclosed and claimed invention may be attached to any of various functional moieties. A T cell receptor mimic of the presently disclosed and claimed invention attached to a functional moiety may be referred to herein as an "immunoconjugate". In one embodiment, the functional moiety is a detectable moiety or a therapeutic moiety.

As is described and demonstrated in further detail hereinbelow, a detectable moiety or a therapeutic moiety may be particularly employed in applications of the presently disclosed and claimed invention involving use of the T cell receptor mimic to detect the specific peptide/MHC complex, or to kill target cells and/or damage target tissues.

The presently disclosed and claimed invention include the T cell receptor mimics described herein attached to any of numerous types of detectable moieties, depending on the application and purpose. For applications involving detection of the specific peptide/MHC complex, the detectable moiety attached to the T cell receptor mimic may be a reporter moiety that enables specific detection of the specific peptide/MHC complex bound by the T cell receptor mimic of the presently disclosed and claimed invention.

While various types of reporter moieties may be utilized to detect the specific peptide/MHC complex, depending on the application and purpose, the reporter moiety may be a fluorophore, an enzyme or a radioisotope. Specific reporter moieties that may utilized in accordance with the presently disclosed and claimed invention include, but are not limited to, green fluorescent protein (GFP), alkaline phosphatase (AP), peroxidase, orange fluorescent protein (OFP), β-galactosidase, fluorescein isothiocyanate (FITC), phycoerythrin, Cy-chrome, rhodamine, blue fluorescent protein (BFP), Texas red, horseradish peroxidase (HPR), and the like.

The presently disclosed and claimed invention includes the T cell receptor mimics described herein attached to any of numerous types of therapeutic moieties, depending on the application and purpose. Various types of therapeutic moieties that may be utilized in accordance with the presently disclosed and claimed invention include, but are not limited to, a cytotoxic moiety, a toxic moiety, a cytokine moiety, a bi-specific antibody moiety, and the like. Specific examples of therapeutic moieties that may be utilized in accordance with the presently disclosed and claimed invention include, but are not limited to, small molecules, peptides, lipids, carbohydrates, nucleic acids or other molecules organic or inorganic, that are used to treat one or more of the following conditions after crossing the blood-brain-barrier (often also described as microvascular permeability) including: neurodegenerative disorders, such as cerebrovascular accidents (CVA), Alzheimer's disease (AD), vascular-related dementia, Creutzfeldt-Jakob disease (CJD), bovine spongiform encephalopathy (BSE), Parkinson's disease (PD), brain trauma, multiple sclerosis (MS), amyotrophic lateral sclerosis (ALS), Huntington's chorea; peripheral disorders with a CNS component, such as septic shock, hepatic encephalopathy, (diabetic) hypertension, diabetic microangiopathy, sleeping sickness, Whipple disease, and Duchenne muscular dystrophy; neuropsychiatric disorders, such as depression, autism, anxiety attention deficit hyperactivity disorder (ADHD), neuropsychiatric systemic lupus erythematosus, bipolar disorder, schizophrenia and other psychoses; other CNS disorders, such as brain tumors, epilepsy, migraine, narcolepsy, insomnia, chronic fatigue syndrome, mountain sickness, encephalitis, meningitis, and AIDS-related dementia.

A pharmaceutical composition of the presently disclosed and claimed invention includes a T cell receptor mimic of the presently disclosed and claimed invention and a therapeutic moiety conjugated thereto that specifically targets the BBB. The pharmaceutical composition of the presently disclosed and claimed invention may be an antineoplastic agent. A diagnostic composition of the presently disclosed and claimed invention includes a T cell receptor mimic of the presently disclosed and claimed invention and a detectable moiety conjugated thereto.

Such therapeutic agents or active agents that can be conjugated to the TCR mimics of the present invention include, e.g., anti-tumor compounds, such as antineoplastic agents or cytotoxic drugs, such as alkylating agents, e.g., Mechlorethamine hydrochloride (Nitrogen Mustard, Mustargen, HN2), Cyclophosphamide (Cytovan®, Endoxana®), Ifosfamide Chlorambucil (Leukeran®), Melphalan (Phenylalanine Mustard, L-sarcolysin, Alkeran®, L-PAM), Busulfan (Myleran®), Thiotepa (Triethylenethiophosphoramide), Carmustine (BiCNU, BCNU), Lomustine (CeeNU, CCNU), Streptozocin (Zanosar®); plant alkaloids, e.g., Vincristine (Oncovin®), Vinblastine (Velban®, Velbe®), Paclitaxel (Taxol®), and the like; antimetabolites, e.g., methotrexate (MTX), Mercaptopurine (Purinethol®, 6-MP), Thioguanine (6-TG), Fluorouracil (5-FU), Cytarabine (Cytosar-U®®, Ara-C), Azacitidine (Mylosar®, 5-AZA) and the like; antibiotics, e.g., Dactinomycin (Actinomycin D, Cosmegen®), Doxorubicin (Adriamycin®), Daunorubicin (Daunomycin®, Cerubidine®), Idarubicin (Idamycin®), Bleomycin (Blenoxane®), Picamycin (Mithramycin®, Mithracin®), Mitomycin (Mutamycin®) and the like, and other anticellular proliferative agents, e.g., Hydroxyurea (Hydrea®), Procarbazine (Mutalane®), Dacarbazine (DTIC-Dome®), cisplatin (Platinol®), Carboplatin (Paraplatin®), Asparaginase (Elspar®), Etoposide (VePesid®, VP-16-213), Amsarcrine (AMSA, m-AMSA), Mitotane (Lysodren®), Mitoxantrone (Novatrone®), and the like; gefitinib (ZD1839 or Iressa®) and imatinib mesylate (Gleevec® or Glivec®); anti-cancer biopharmaceutical drugs including antibodies (Rituxan® or rituximab; Herceptin® or trastuzumab; Zevalin® or ibritumomab tiuxetan (radiolabeled); Erbitux® or cetuximab; Avastin™ or bevacizumab or rhuMAb-VEGF) and cytokines (Intron® or α-interferon; Proleukin® IL-2 or aldesleukin) to treat primary brain tumors or brain metastasis of somatic tumors; anti-inflammatory drugs including antibodies (Enbrel® or etanercept; Remicade® or infliximab; Simulect® or basiliximab; Zenapax® or daclizumab; Kineret® or anakinra; Xolair® or omalizumab; Humira® or adalimumab; Antegren® or natalizumab; RhuFab™ or ranibizumab; Raptiva™ or efalizumab) and cytokines such as interferon-α, interferon-β (Avonex® or interferon β-1a; Betaseron®/Betaferon® or interferon β-1b; Rebif® or interferon-β-1a), interferon-γ interleukin 1 (IL-1), interleukin 2 (IL-2), interleukin 3 (IL-3), interleukin 4 (IL-4), interleukin 5 (IL-5), interleukin 6 (IL-6), TNF, granulocyte macrophage colony stimulating factor (GM-CSF: Leukine® or sargramostim), granulocyte colony stimulating factor (G-CSF: Neupogen® or filgrastim), macrophage colony stimulating factor (M-CSF), platelet-derived growth factor (PDGF). The therapeutic agents or active agents can be used to treat e.g., neuroinflammation related to neurodegenerative disorders; neurotrophic factors (e.g., NGF or nerve growth factor; BDNF or brain-derived neurotrophic factor; NT3 or neurotrophin-3; NT4 or neurotrophin-4; NT5 or neurotrophin-5; RDGF or retina-derived growth factor; CNTF or ciliary neurotrophic factor; activin; bFGF or basic fibroblast growth factor; aFGF or acidic fibroblast growth factor; GDNF or glial cell line-derived neurotrophic factor or neublastin or artemin or enovin, presephin, neurturin; CTGF or connective tissue growth factor; EGF or epithelial growth factor); erythropoietins (EPO) (Procrit®/Eprex® or erythropoietin alfa; Epogen® or erythropoietin; NeoRecormon® or erythropoietin β; Aranesp® or darbepoietin alfa); growth hormone or somatotropin (Humatrope®; Protropin®/Nutropin®; Serostim®; Saizen®); anti-NogoA Mab (IN-1); NogoA antagonist of Nogo66 inhibitor (NEP1-40).

Other therapeutic agents or active agents can be used to treat, e.g., neurodegenerative disorders; enzymes (e.g., Cerezyme® or glucocerebrosidase; Aldurazyme™ or laronidase; Aryplase™ or arylsulfatase B; 12S or iduronate-2-sulfatase; α-L-iduronidase; N-acetylgalactosamine 4-sulfatase; phenylase; aspartylglucosaminidase; acid lipase; cysteine transporter; Lamp-2; a galactosidase A; acid ceramidase; α-L-fucosidase; ss-hexosaminidase A; GM2-activator deficiency; α-D-mannosidase; ss-D-mannosidase; arylsulfatase A; saposin B; neuraminidase; α-N-acetylglucosaminidase phosphotransferase; phosphotransferase 7-subunit; heparan-N-sulfatase; α-N-acetylglucosaminidase; acetyl-CoA: N-acetyltransferase; N-acetylglucosamine 6-sulfatase; galactose 6-sulfatase; β-galactosidase; hyaluronoglucosaminidase; multiple sulfatases; palmitoyl protein thioesterase; tripeptidyl peptidase I; acid sphingomyelinase; cholesterol trafficking; cathepsin K; α-galactosidase B; sialic acid transporter; SOD or Cu/Zn superoxide dismutase) to treat e.g., (neurological symptoms related to) lysosomal storage diseases or other neurodegenerative disorders; brain-acting hormones and neurotransmitters such as somatostatin, oxytocin, vasopressin, guaranine, VIP, adrenocorticotropic hormone (ACTH), cholecystokinin (CCK), substance-P, bombesin, motilin, glicentin, glucagon, glucagon-like peptide (GLP-1); and neuropeptides and derivatives thereof such as peptide YY (PYY), neuropeptide Y (NPY), pancreatic polypeptide (PP), neurokinin A, neurokinin B, endorphin, enkephalin, neurotensin, neuromedin K, neuromedin L, calcitonin related peptide (CGRP), endothelin, ANP ("atrial natriuretic peptide"), BNP ("brain natriuretic peptide"), CNP (C-type natriuretic peptide"), and PACAP ("pituitary adenylate cyclase activating peptide").

Other active agents can be used to treat imaging agents.

Other therapeutic agents or active agents can be neurotransmitter antagonists or agonists that do not penetrate the blood-brain barrier (such as certain NMDA receptor blockers); antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; β-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4-diaminopyrimidines, nitrofurans, quinolones and analogs thereof, sulfonamides, sulfones; antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazole, e.g., fluconazole, itraconazole, terconazole; anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.; antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanyl, gentiopicrin, halofantrine, hydroxychloroquine, mefloquine hydrochloride, 3-methylarsacetin, pamaquine, plasmocid, primaquine, pyrimethamine, quinacrine, quinine, quinine, quinocide, quinine, dibasic sodium arsenate; antiprotozoal agents, such as: acranil, timidazole, ipronidazole, ethylstibamine, pentamidine, acetarsone, aminitrozole, anisomycin, nifuratel, timidazole, benzidazole, suramin.

Other therapeutic agents or active agents can be genes (including expression vectors and/or promoters, preferably the GFAP and/or GTP promoters) encoding for polypeptides, proteins, peptides, enzymes, cytokines, interleukins, hormones and growth factors described herein above) or antisense DNA for polypeptides; and antisense probes (nucleic acids or peptide nucleic acids).

In addition to direct conjugation between the therapeutic or diagnostic moieties and the targeting agent, such therapeutic or diagnostic moieties may be conjugated either directly or via any of the well-known polymeric conjugation agents such as sphingomyelin, polyethylene glycol (PEG) or other organic polymers, and either with a single targeting agent or in combination with any of the well-known blood-brain barrier targeting moieties against the insulin, transferrin, IGF, leptin, LRP (1B) or LDL receptor on the blood-brain barrier and brain cell membrane.

The presently disclosed and claimed invention relates to methodologies for utilizing an agent, such as but not limited to antibodies or antibody fragments that function as T-cell receptor mimics (TCRm's), that recognize peptides displayed in the context of HLA molecules, wherein the peptide is associated with a tumorigenic, infectious, disease or immune dysfunction state at the BBB. These antibodies will mimic the specificity of a T cell receptor (TCR) such that the molecules may be used as therapeutic reagents. In one embodiment, the T cell receptor mimics of the presently disclosed and claimed invention will have a higher binding affinity than a T cell receptor. In one embodiment, the T cell receptor mimic produced by the method of the presently disclosed and claimed invention has a binding affinity of about 10 nanomolar or greater.

In one embodiment, the methods utilize a T-cell receptor mimic, as described in detail hereinabove and in U.S. Ser. No. 11/809,895, filed Jun. 1, 2007, and in US Published Application Nos. US 2006/0034850, filed May 27, 2005, and US 2007/00992530, filed Sep. 7, 2006, and 20090304679 filed Feb. 27, 2009, incorporated herein by reference. The T-cell receptor mimic utilized in the methods of the presently disclosed and claimed invention comprises an antibody or antibody fragment reactive against a specific peptide/MHC complex, wherein the antibody or antibody fragment can differentiate the specific peptide/MHC complex from the MHC molecule alone, the specific peptide alone, and a complex of MHC and an irrelevant peptide. The T cell receptor mimic may be produced by any of the methods described in detail in the patent applications listed herein above and expressly incorporated herein by reference; for example but not by way of limitation, the T cell receptor mimic may be produced by immunizing a host with an effective amount of an immunogen comprising a multimer of two or more specific peptide/MHC complexes.

In one embodiment, the T cell receptor mimic may be produced by a method that includes identifying a peptide of interest, e.g., a peptide expressed only in epithelial cells of the BBB or that are only expressed by those cells upon the initiation of a disease or disease condition, wherein the peptide of interest is capable of being presented by an MHC molecule, and wherein the vaccine composition comprises the peptide of interest. An immunogen comprising a multimer of two or more peptide/MHC complexes is then formed, wherein the peptide of the peptide/MHC complex is the peptide of interest. An effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced, wherein the desired antibodies can differentiate the peptide/MHC complex from the MHC molecule alone, the peptide of interest alone, and a complex of MHC and irrelevant peptide. The desired antibodies are then isolated.

Peptides that have been utilized to produce TCRm's by the methods described in detail in U.S. Ser. No. 11/809,895, filed Jun. 1, 2007, and in US Published Application Nos. US 2006/0034850, filed May 27, 2005, and US 2007/00992530, filed Sep. 7, 2006, and 20090304679 filed Feb. 27, 2009, are incorporated herein by reference. The use of TCRm's produced using any of the peptides of SEQ ID NOS: 1-97 disclosed in the above-referenced patent applications, each of which are incorporated herein by reference. However, it is to be understood that the presently disclosed and claimed invention is not limited to TCRm's produced using the peptides, but rather the scope of the presently disclosed and claimed invention encompasses TCRm's raised against any specific peptide/MHC complex.

T-cell receptor mimics (TCRm) are a novel class of monoclonal antibodies with binding characteristics resembling T cell receptors (Weidanz et al., 2006; Weidanz et al., 2007). In particular, binding specificity is determined by the MHC molecule in combination with a peptide presented in its binding groove. TCRm are currently evaluated both as diagnostic tools and as therapeutics in a variety of settings, e.g. for assessment of vaccine potency and as anti-tumor agents (Neethling et al., 2008; Verma et al., 2010; Verma et al., 2010).

The present document introduces a novel field of application for TCRm. The inventors have recently shown that TCRm bind to specific peptide-MHC targets on human brain derived endothelial cells and undergo internalization (Bhattacharya et al., 2010). Therefore, TCRm have the potential to be useful as vascular targeting agents. The present invention shows that its possible to identify peptide-MHC complexes on vascular endothelial cells of a given organ (e.g., brain), TCRm are generated that target such peptide-MHC complexes with high specificity and avidity. It is demonstrated herein in vitro and in vivo that the TCRm-active agent binding to a monolayer of brain-derived endothelial cells and time dependent, saturable transcytosis with a prototype TCRm, RL-6A. RL-6A recognizes a specific peptide-HLA-A2 complex derived from p68 RNA helicase (Verma et al., 2010). Further, it is shown here with an in vivo model, transgenic mice expressing human HLA-A2, that the TCRm antibody targets brain. The endothelial cells of blood vessels in the central nervous system (CNS) form the blood-brain barrier (BBB), which is currently a major obstacle to the development of drugs for diverse diseases affecting the CNS, including neurodegenerative diseases (e.g. Alzheimer's Disease, Parkinson Disease), neuroinflammatory disorders (e.g. Multiple Sclerosis, ischemia/reperfusion injury associated with stroke), and primary or metastatic brain tumors. The present invention is an efficient and specific targeting tool that allows delivery of diagnostic agents and active agents (e.g., drugs) to the CNS is an unmet need and will have broad impact.

EXAMPLE 1

Demonstration of RL-6A Transcytosis Using an In Vitro Model of the Blood-Brain Barrier Radiolabeling of Antibodies: Either of the monoclonal antibodies, RL6A (as described in detail hereinabove and in U.S. Ser. No. 11/809,895, filed Jun. 1, 2007, and in US Published Application Nos. US 2006/0034850, filed May 27, 2005, and US 2007/00992530, filed Sep. 7, 2006, and 20090304679 filed Feb. 27, 2009, incorporated herein by reference), BB7.2 (ATCC Accession No. HB-82) and UPC10 (isotype control lgG2a, Sigma Aldrich) was labeled with Na $^{125}$I from Perkin Elmer (Waltham, Mass., USA) using a chloramine-T method. Briefly, 1 mCi Na $^{125}$I was reacted with 401 Jg antibody in 5-20 μl phosphate buffered saline (pH 7.4), and was incubated at room temperature for 1 min 0.51 μg/5 μl chloramine-Tin phosphate buffer, and following 1 min incubation with additional 0.255 μg/2.5 μl chloramine-T. The reaction was stopped by adding 3.2 μg/10μ sodium metabisulfite (SigmaAldrich, St. Louis, Mo.). Labeled antibody was purified using a PD-10 SEP-HADEX™ G25M gel filtration column (GE healthcare Piscataway, N.J.), with an elution 0.02M sodium phosphate buffer in 0.9% NaCl (pH7.4). The peak fractions were pooled and stored at −80° C. for use in the subsequent experiments. Each antibody was labeled to a specific activity of 12.5 μCi/μg (1875 μCi/nmole) and a trichloroacetic acid (TCA) precipitability of >99%. In vitro studies with endothelial cells: Two immortalized human brain derived endothelial cell lines were used: hCMEC/D3 (Weksler et al., 2005) and HH8 (Koval A, Shah, K, Abbruscato, T J, Generation of a New, Highly Restrictive, Conditionally Immortalized Human Brain Microvascular Endothelial Cell Line. Society of Biomolecular Sciences 16th Annual Conference & Exhibition, Advancing the Science of Drug Discovery, Phoenix, Ariz., Apr. 11-15, 2010). Cells were grown on type 1 collagen pre-coated transwell filters after seeding at a density of 100,000 cells/cm$^2$. hCMEC/D3 cells are grown at 37° C. throughout, while HH8 are temperature sensitive and grow at 33° C. After confluence the HH8 monolayer is kept at 37° C. for 48 h before the binding/transport experiments. Half of the assay media was changed after 4-7 days and transport assays were performed within 8-10 days after seeding. INFγ (20 ng/ml) was added 24 h-72 h before assay to stimulate MHC class I expression and processing. To qualify p68 peptide-MHC class I expression, both cell lines with and without addition of IFNγ were stained with RL-6A and target expression was evaluated using flow cytometric analysis.

Cell binding and transport assays: Radiolabeled antibodies $^{125}$I-RL-6A, 1251-BB7.2 (pan-HLA A2), or $^{125}$I-UPC-10 at a concentration of 5×10$^6$ cpm/0.5 ml (~2 nM), in presence or absence of a >100-fold molar excess of unlabeled antibody of the same type, were added to the upper chamber of transwells and incubated with the endothelial cells at 37° C. At 15, 30, 60, and 120 min, 50 μl samples from the lower chamber were withdrawn for gamma counting and replaced with an equal volume of fresh assay medium. At the end of the incubation, cells were washed carefully, and cell-associated radioactivity was determined by removing the membranes of the culture insert and counting it in a gamma-counter. For the measurement of acid resistant binding, wash steps were performed with glycine buffer at pH 3.

Binding data were expressed as cpm bound per filter. Transendothelial transport data were expressed as time-dependent volume cleared from the upper chamber. Linear regression was applied to fit the time course data and slopes between the different antibodies were statistically compared using GraphPad Prism 5.0

EXAMPLE 2

Brain Uptake of RL6A in HLA-A2 Transgenic Mice Pharmacokinetics in HLA-A2 Transgenic Mice Two HLA-A2 transgenic mouse strains expressing different constructs of human A*0201 were obtained from Jackson labs (Bar Harbor, Me.): C57BL/6-Tg(HLA-A2.1)1 Enge/J [stock #3475]; and B6.Cg-Tg(HLA-A/H2-D) 2Enge/J [stock #4191]. All animal experiments were performed according to NIH guidelines and were approved by the institutional animal care and use committee at Texas Tech University Health Sciences Center. Mice were kept under controlled temperature, light (12 h dark/12 h light cycle) and humidity and were fed standard rodent chow. Next, 2-6 month old transgenic mice (weight range 20-25 grams) were used naïve or after receiving intra-peritoneal (IP) injections of interferon gamma (IFNγ) at a dose of 10,000 U/animal in saline two times with a 24 h interval. Pharmacokinetic experiments were started 48 h after the first IFNγ injection. For the pharmacokinetic studies, animals were kept under continuous anesthesia with 1-1.5% isoflurane in $N_2O:O_2$ (70:30 volume %) throughout the experiments. The right common carotid artery was catheterized with PE-10 in retrograde direction for repeated blood sampling. The tracers were labeled as described under "Methods" in EXAMPLE 1 and injected i.v. into the jugular vein (70 μL in 10 mM Na-phosphate/0.15 M NaCl (pH7.4). An aliquot (30 ul) of blood was collected at predetermined time intervals of 1, 5, 10, 20, 30, 40 and 60 min from the PE-10 cannula inserted in the common carotid artery. For control antibody UPC10, the pharmacokinetic sampling was done for up to 2 h. The sample volume was replaced through the carotid cannula with saline containing heparin (100 U/ml). At 60 min after injection, the mice were euthanized and organs (brain, heart, lung, liver, kidney, spleen) were collected and weighed. Blood samples from each time point, were centrifuged for collection of plasma (8,600×g for 3 minutes).

Radioactivity of 5 μl aliquots of blood and plasma and of the organ samples was measured using automatic gamma counter 2470 (Perkin Elmer Life and Analytical Sciences, Waltham, Mass., USA). The radioactivity concentration (cpm/g) was converted to percentage of injected dose (% ID/g for organs; % ID/ml for blood and plasma), and the organ distribution values were corrected for the corresponding vascular volume of each organ using the equation $$C_{organ} = (V_D - V_o) \times C_{pl}(T)$$

Where $V_D$ is the apparent organ volume of distribution at sampling time T, $V_0$ is the plasma volume of the corresponding organ and $C_{p1}(T)$ equals plasma concentration at time T. Pharmacokinetic parameters describing the time course of plasma or blood concentrations were determined by fitting concentration-time data to a biexponential equation, $$C = C_1 e^{-\lambda_1 t} + C_2 e^{-\lambda_2 t}$$

using nonlinear regression in Scientist 3.0 (Micromath Research, Saint Louis, Mich.). Derived parameters were calculated according to standard pharmacokinetic equations.

Brain Capillary depletion: To determine the extent of transcytosis of the antibodies in vivo, a capillary depletion method was used as previously described (Lee et al., 2000). Briefly, cerebral hemispheres were collected from the animals after pharmacokinetic sampling for 60 minutes after IV injection of $^{125}I$ MAb. The collected hemispheres were weighed and homogenized on ice in cold physiological buffer (10 mM HEPES, 141 mM NaCl, 4 mM KCl, 2.8 mM $CaCl_2$, 1 mM $MgSO_4$, and 10 mM D-glucose, pH7.4) with a glass tissue grinder, followed by the addition of cold dextran solution to a final concentration of 16%. After removal of an aliquot of the homogenate, the remainder was centrifuged at 4,300×g for 15 m in at 4° C. and the supernatant was carefully separated from the capillary pellet. The capillary pellet was re-suspended in 0.5 ml physiological buffer. Radioactivity was measured in the aliquots of homogenate and postvascular supernatant and in the re-suspended capillary pellet.

Acid Precipitation: To determine the integrity of the radiolabeled antibody, an acid precipitation assay was performed on plasma samples obtained at each time point following IV injection of the antibody; and in brain post-vascular supernatant and capillary pellet after brain capillary depletion. Briefly, 5 μl of the plasma was added to 100 μl of 2.5% BSA; precipitation was performed by additional adding 1 ml of 20% trichloroacetic acid. Similarly capillary pellets resuspended in 500 μl physiological buffer and, 500 μl post-vascular supernatant were subjected to TCA precipitation by adding 500 μl of 20% trichloroacetic acid. After vigorously mixing and incubating 10 min on ice, all samples were centrifuged at 4,000×g for 5 min at 4° C. The supernatant and precipitate were separated and measured in a gamma counter. The results were expressed as the percentage of total radioactivity that precipitated.

Figure 1B:
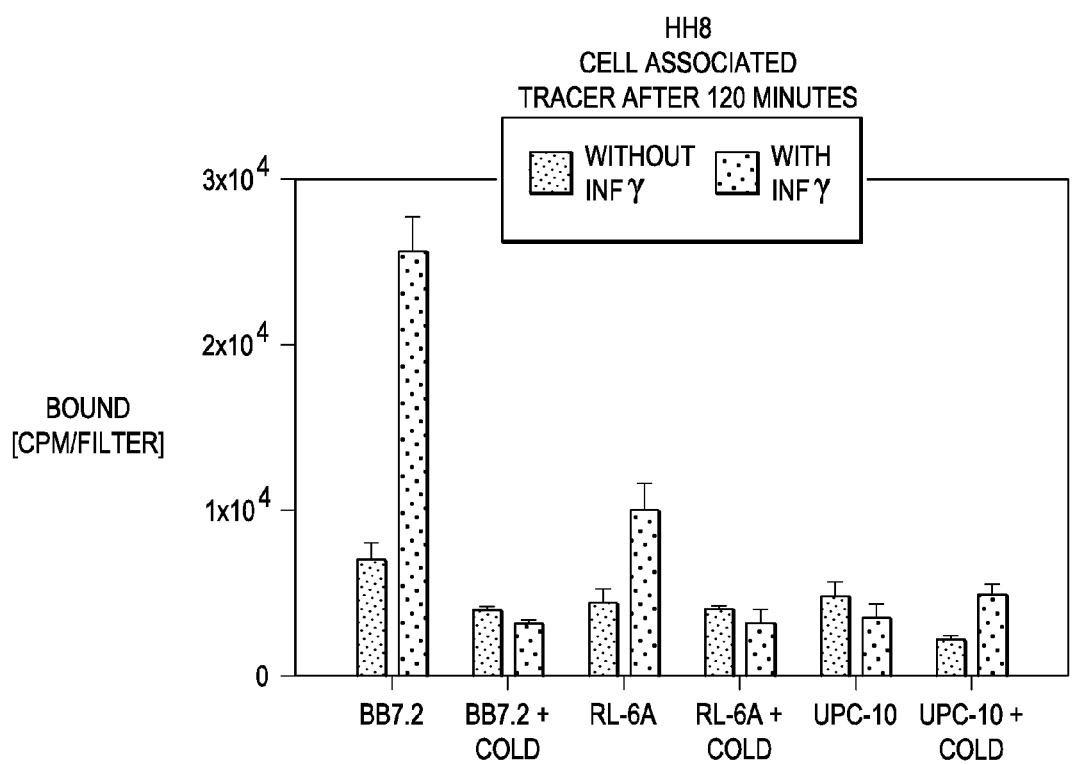
Figure 1C:
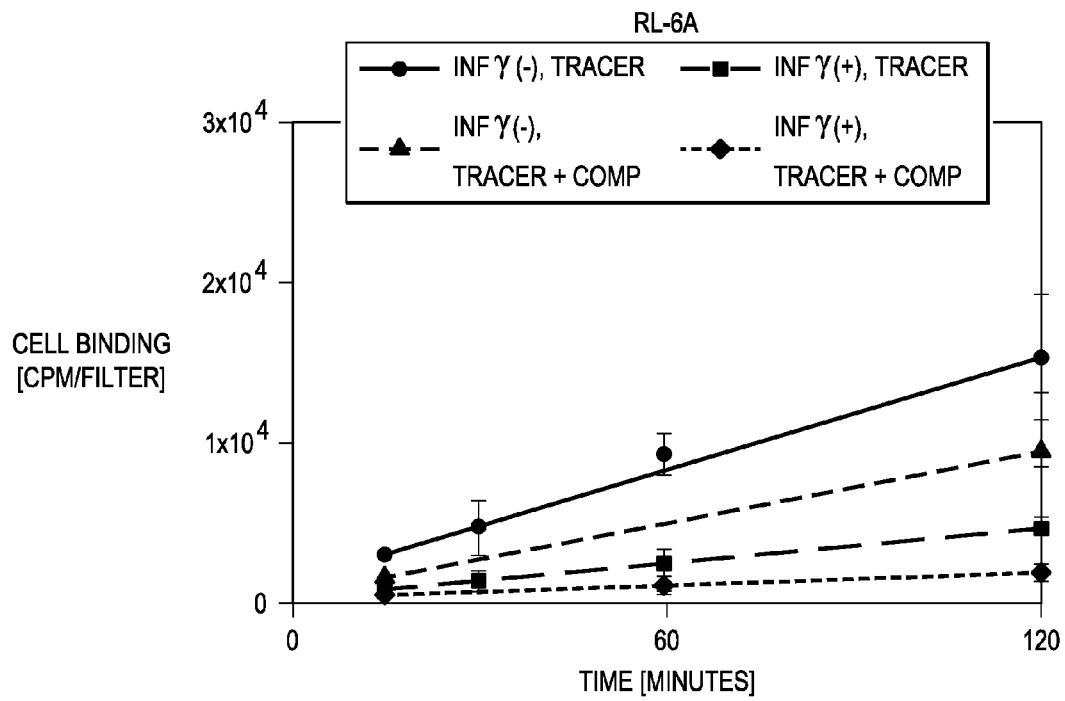
Figure 1D:
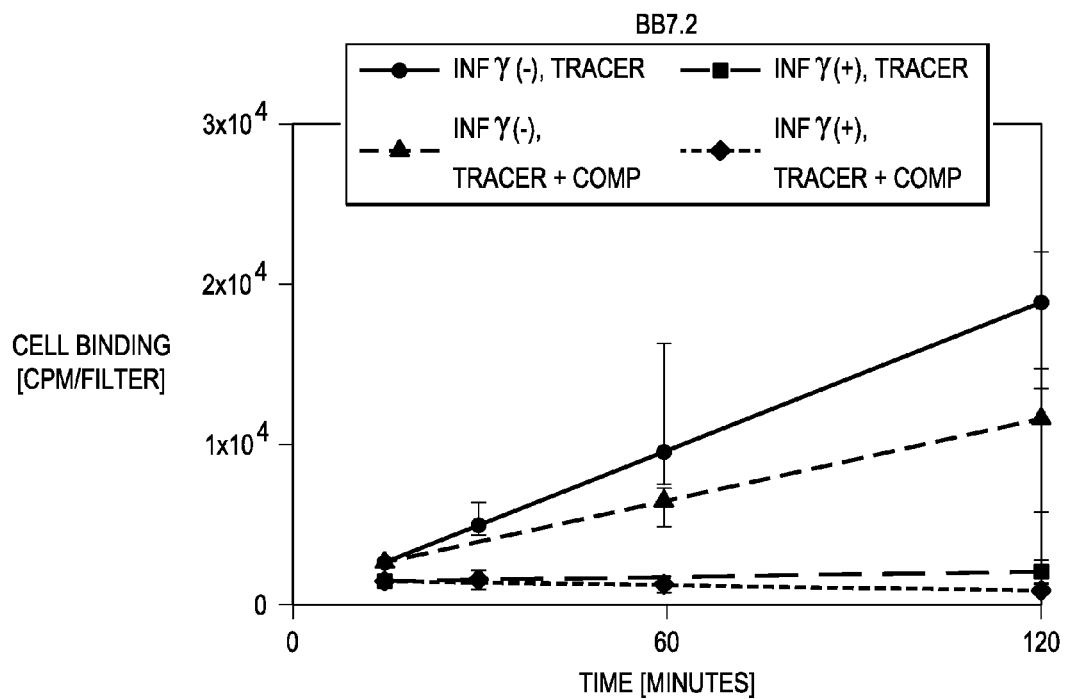
Figure 2A:
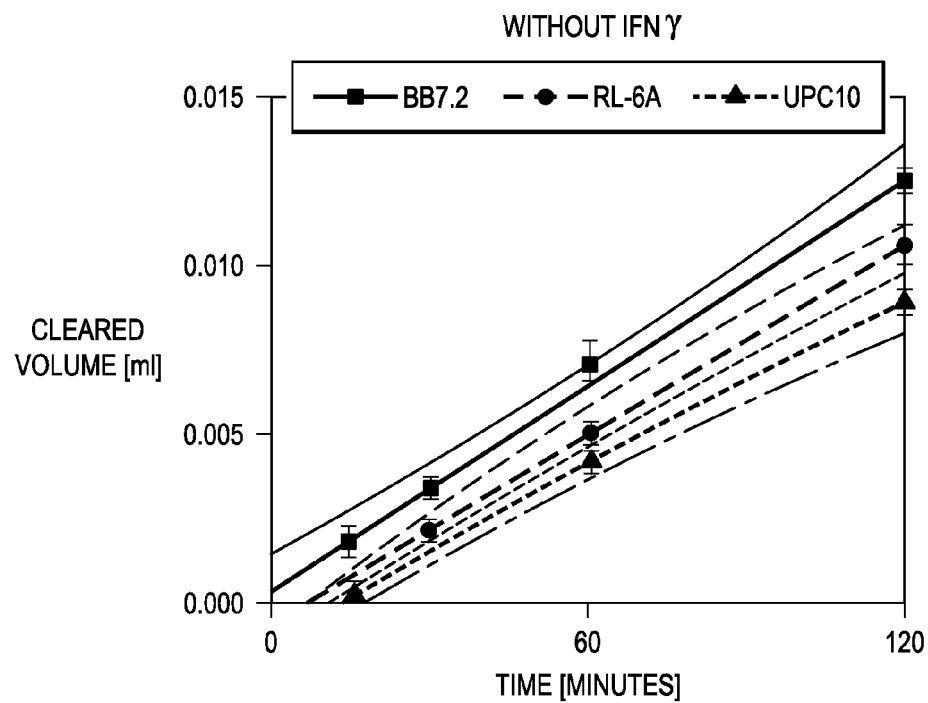
FIGS. 2a-2d. Transcytosis experiments in hCMEC/D3 cells. Linear regression with 95% confidence intervals (dashed lines) was applied to the time course of each antibody. Tracer concentrations were 2 nM, tracer+comp denotes presence of 100-fold molar excess of unlabeled antibody.
Figure 2B:
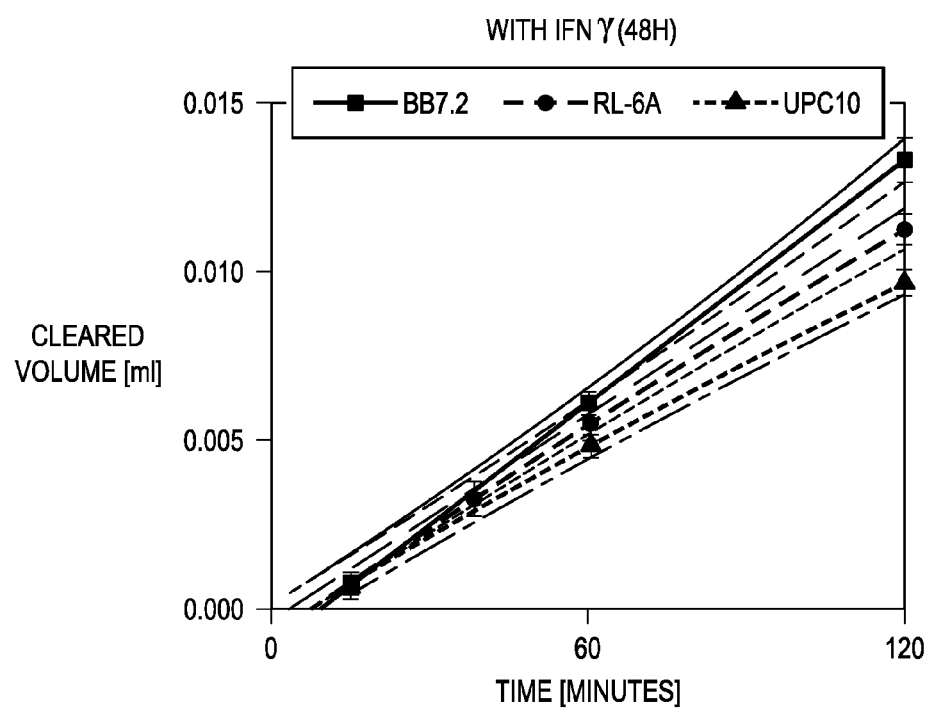
Figure 2C:
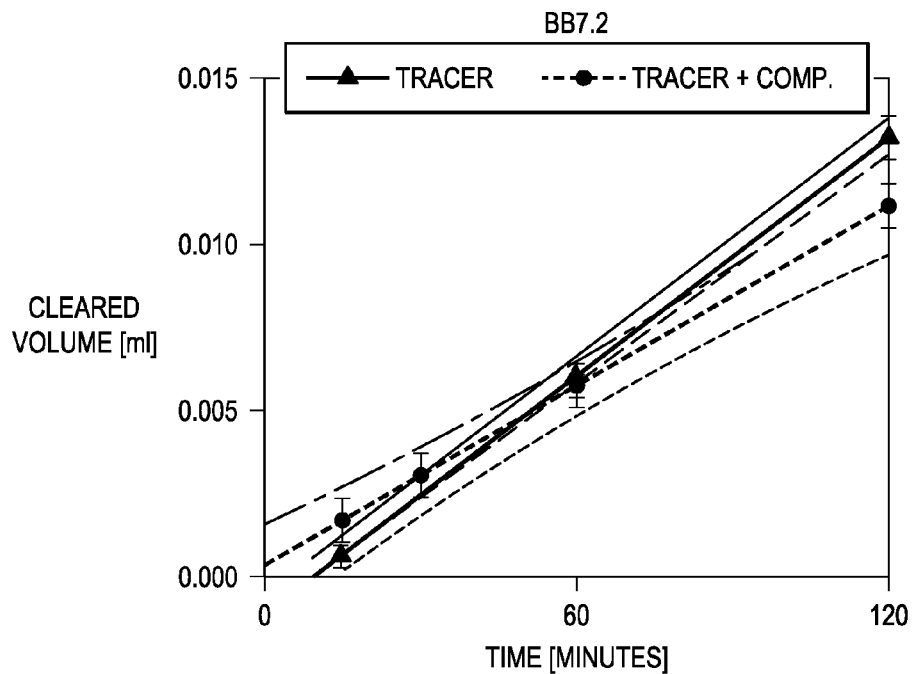
Figure 2D:
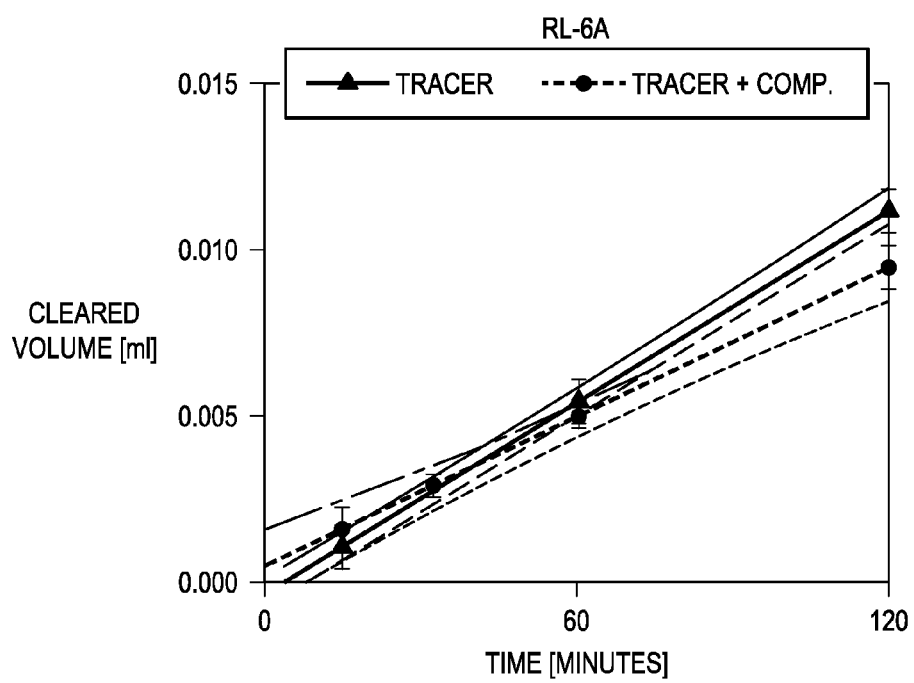
Figure 3A:
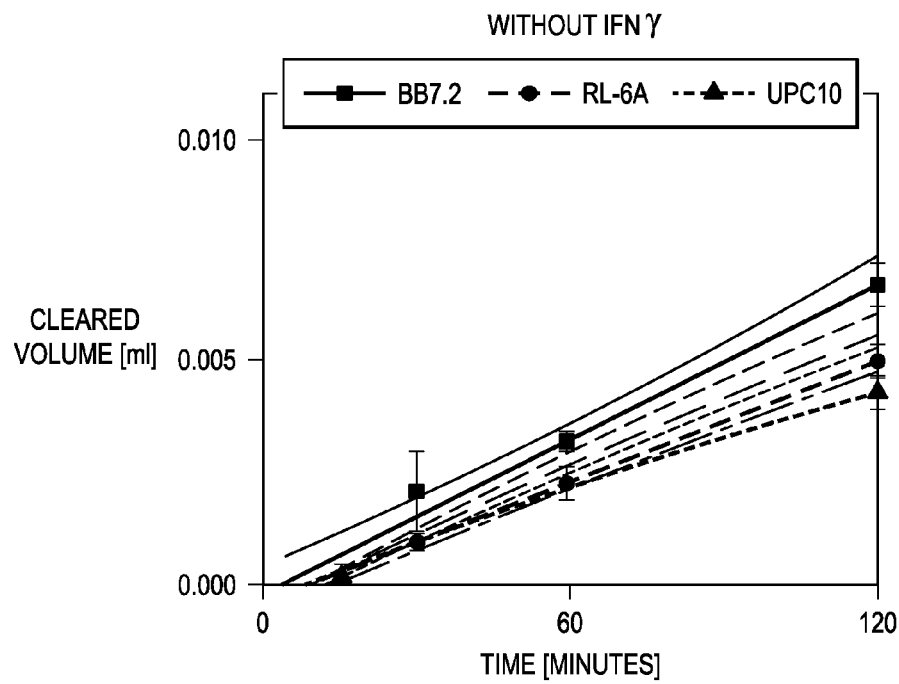
FIGS. 3a-3d. Transcytosis experiments in HH8 cells. Linear regression with 95% confidence intervals (dashed lines) was applied to the time course of each antibody. Tracer concentrations were 2 nM, tracer+comp denotes presence of 100-fold molar excess of unlabeled antibody.
Figure 3B:
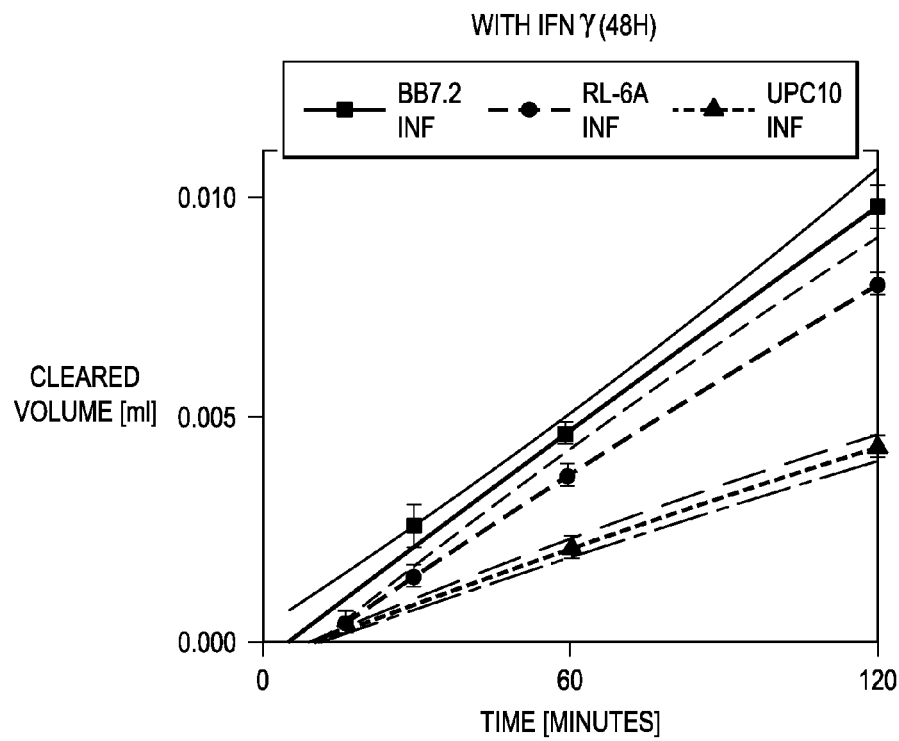
Figure 3C:
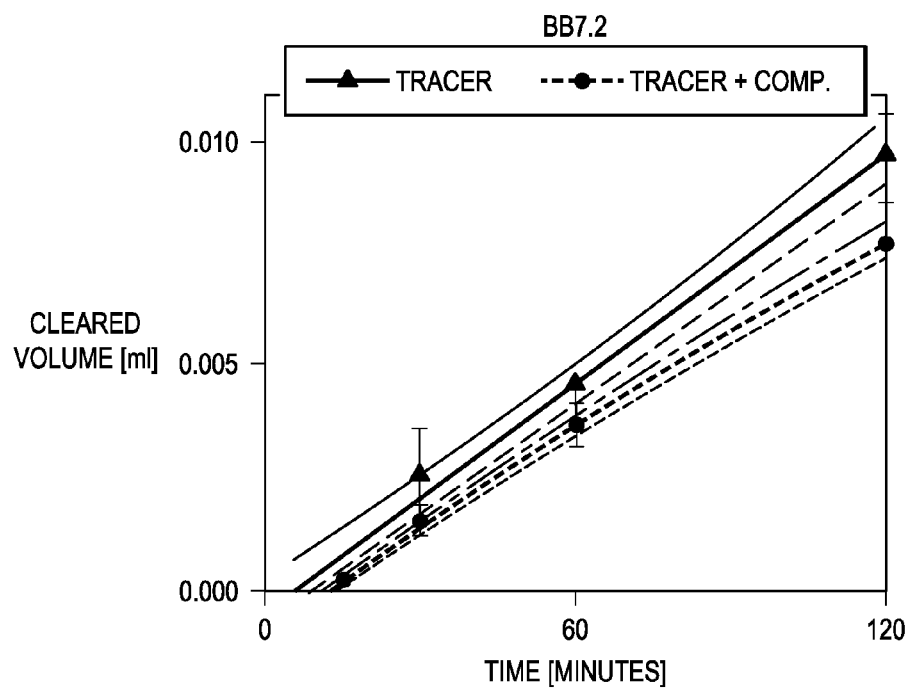
Figure 3D:
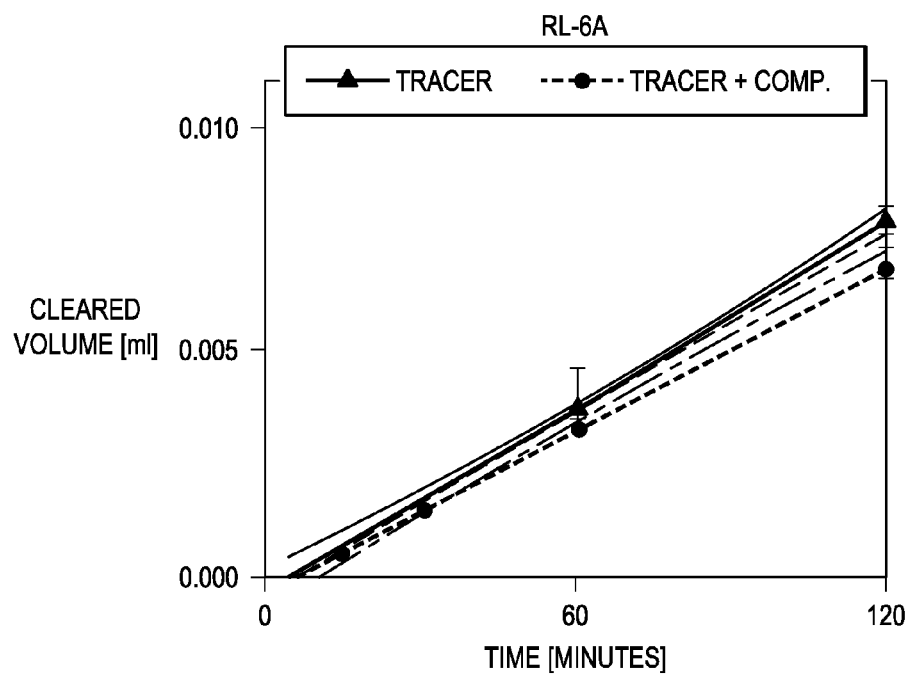

Results from Example 1: The binding of radiolabeled antibodies to hCMEC/D3 and HH8 monolayers after 60 min incubation at 37° C. is shown in FIGS. 1a and 1b. Both cell lines bind RL-6A and BB7.2 in a saturable manner as evident from the decreased binding values in the presence of unlabeled antibody. The binding level under competition by a 100-fold molar excess of the antibody is comparable to the binding of the isotype control UPC-10. Further, binding of BB7.2 and RL6A was enhanced by pretreatment of the cells with IFNγ. The relative increase of RL-6A binding after IFNγ was similar in HH8 and hCMEC/D3 cells, although absolute binding expressed as cpm/filter, was higher in hCMEC/D3 cells. As expected for the pan HLA-A2 antibody BB7.2, its binding values exceeded the corresponding values for RL-6A.

The data on tracer associated with the cell monolayer following mild acid wash in FIGS. 1a -1d demonstrate that both RL-6A (FIG. 1c) and BB7.2 (FIG. 1d) were internalized by hCMEC/D3 cells in a time dependent manner. Consistent with the total binding data (FIGS. 1a and 1b) tracer internalization was almost completely inhibited by competition with unlabeled antibody. As with total cell binding, internalization increased after IFNγ pretreatment of cells.

FIGS. 2a-2d and FIGS. 3a-3d depict the transendothelial transport of antibodies from luminal (upper compartment) to basolateral (bottom compartment). Transfer of UPC-10 tracer as $IgG_{2a}$ isotype control represents paracellular leakage. In naïve cells (without IFNγ stimulation) there were only small differences between RL-6A, BB7.2 and UPC-10. However, after IFNγ the differences increased and both RL-6A and BB7.2 clearance significantly exceeded the clearance of UPC-10. This was expected because treatment of cells with IFNγ increases surface expression of HLA-A2 and the specific target, p68 peptide-HLA-A2. Further, the transendothelial clearance of RL-6A and BB7.2 was significantly decreased by competing unlabeled antibody.

Figure 4A:
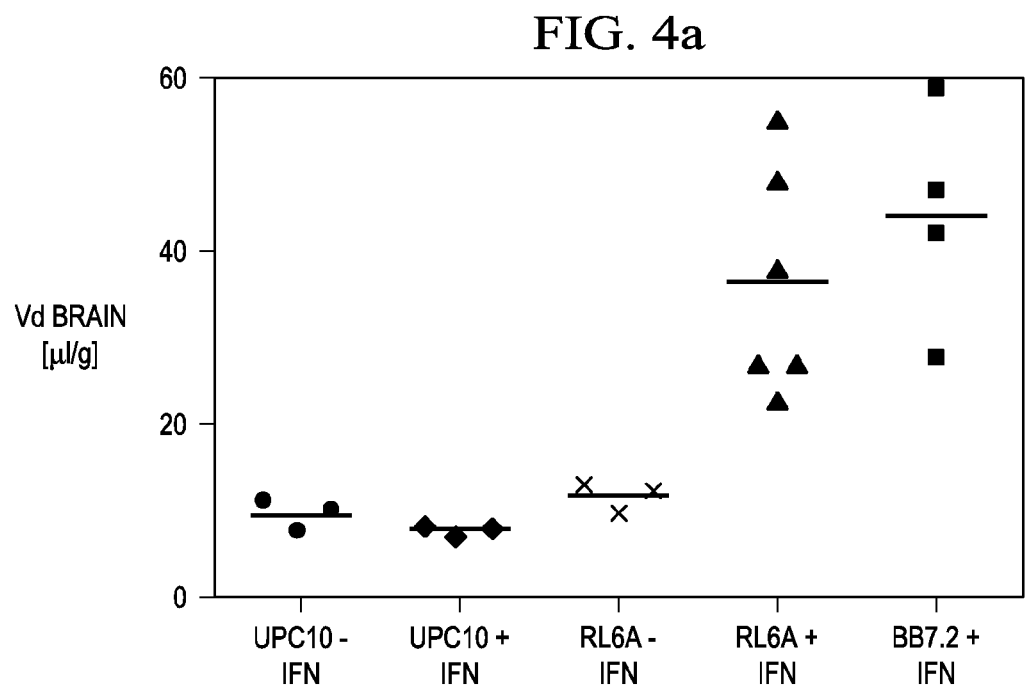
Figure 4B:
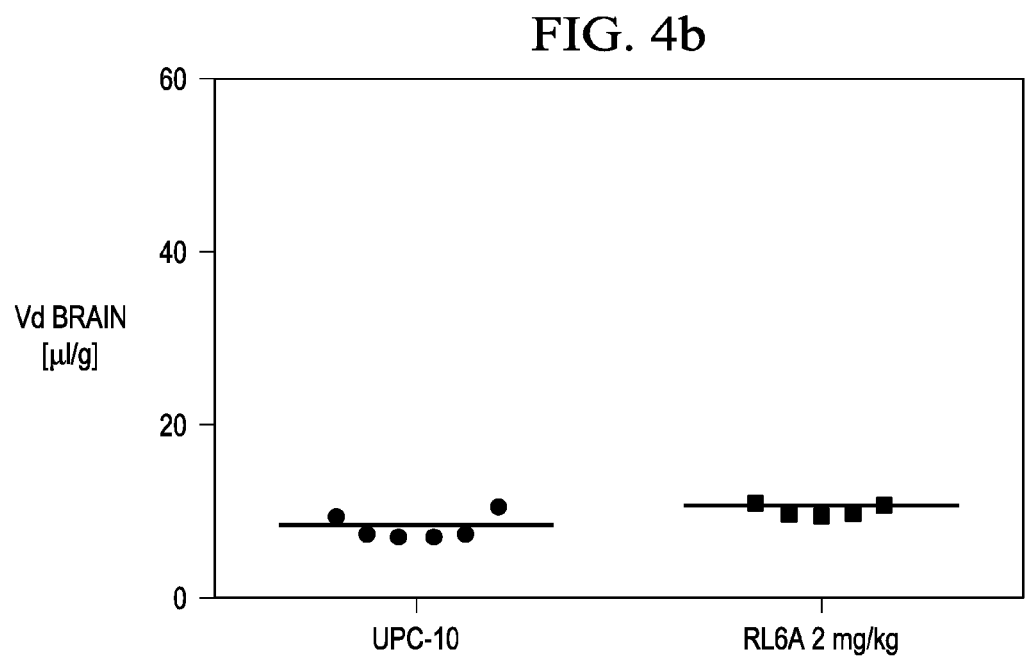

Results from Example 2: The brain uptake of TCRm RL-6A is demonstrated in FIGS. 4a-4d and 5a-5d after intravenous bolus administration of radiolabeled antibody to HLA-A2 transgenic mice of strain 3475 and 4191, respectively. In 3475 mice UPC-10 was used as negative control, representing brain plasma volume. After IFNγ, Vd of both RL-6A and BB7.2 were significantly enhanced over control values (p<0.01 vs. UPC10, ANOVA with Dunnett's post test). Co-injection of an excess (~70 fold) of unlabeled RL-6A decreases Vd brain to the background level (FIG. 4b). The resulting brain concentrations of RL-6A and BB7.2 tracers after correction for vascular space are shown in (FIG. 4c). The result of capillary depletion analysis for R-L6A brain uptake is depicted in (FIG. 4d). More than 50% of tracer present in brain tissue was found in postvascular supernatant, i.e. beyond the BBB, at the sampling time of 60 min.

It was evident that IFNγ treatment in these mice did not cause BBB leakage, as no increase in Vd of the IgG$_{2a}$ isotype control was observed. In this strain the comparison of RL-6A brain uptake with or without IFNγ pretreatment also indicates that basal expression of the target peptide-MHC complex is low. Stimulation of MHC processing and presentation results in significant brain accumulation of RL-6A (0.19±0.03%1D/g) and BB7.2 as shown in FIG. 4c, with the major fraction undergoing transport across the BBB as concluded from capillary depletion (FIG. 4d). The uptake was fully saturated by a dose of 2 mg/kg RL6A (FIG. 4b) further supporting the specificity of the binding and transport mechanism. Similar data were obtained for the strain 4191, expressing a different human HLA-A2 construct.

Figure 5A:
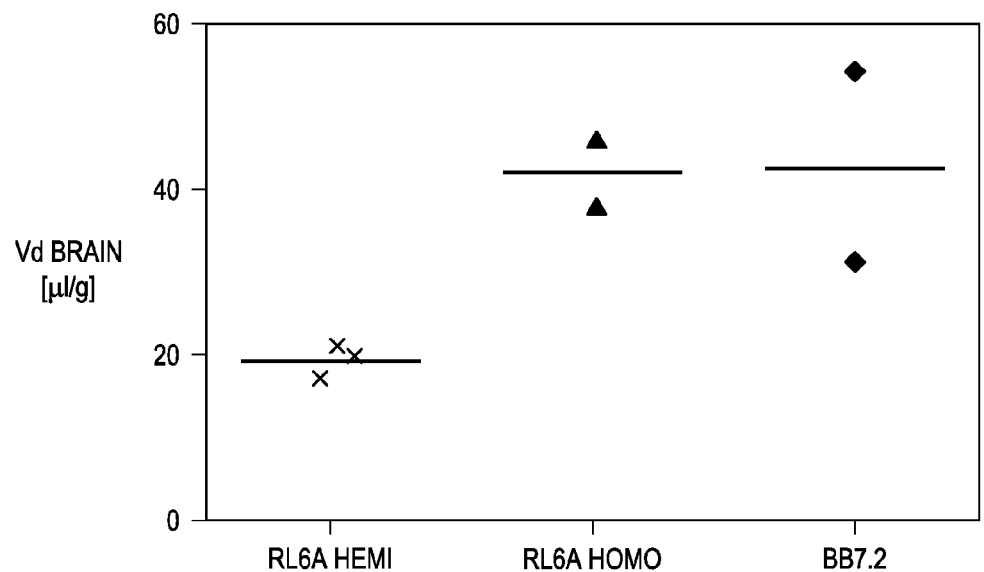
FIGS. 5a-5d. Brain uptake in transgenic mouse strain 4191. Vd brain of RL6A at 60 min after injection is shown in FIG. 5a and FIG. 5c for hemizygous (hemi) or homozygogous (homo) mice. BB7.2 data were obtained in homozygogous animals. All data in FIGS. 5a-5d are from homozygous mice.
Figure 5B:
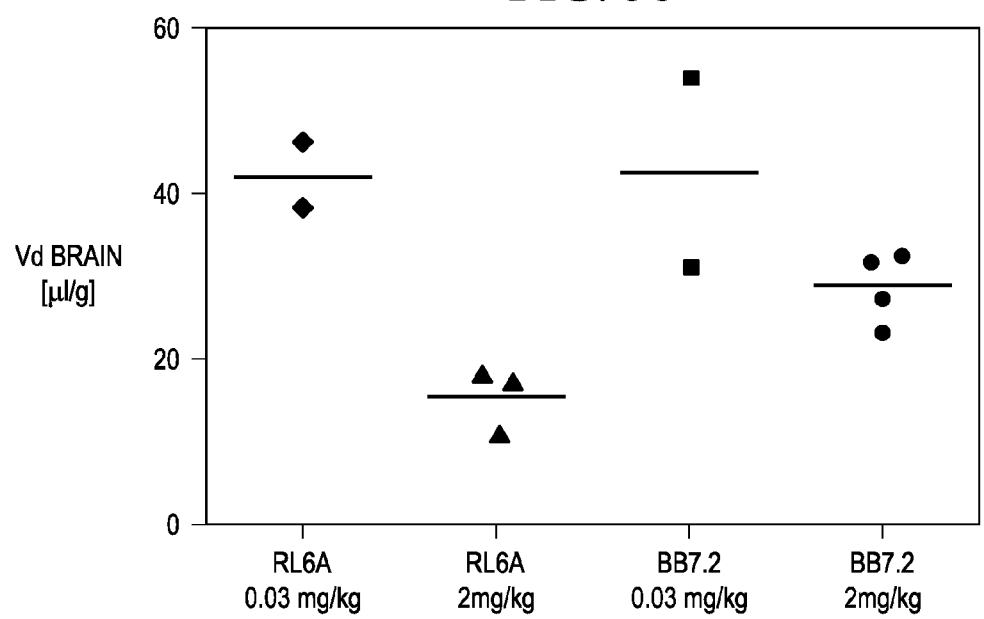
Figure 5C:
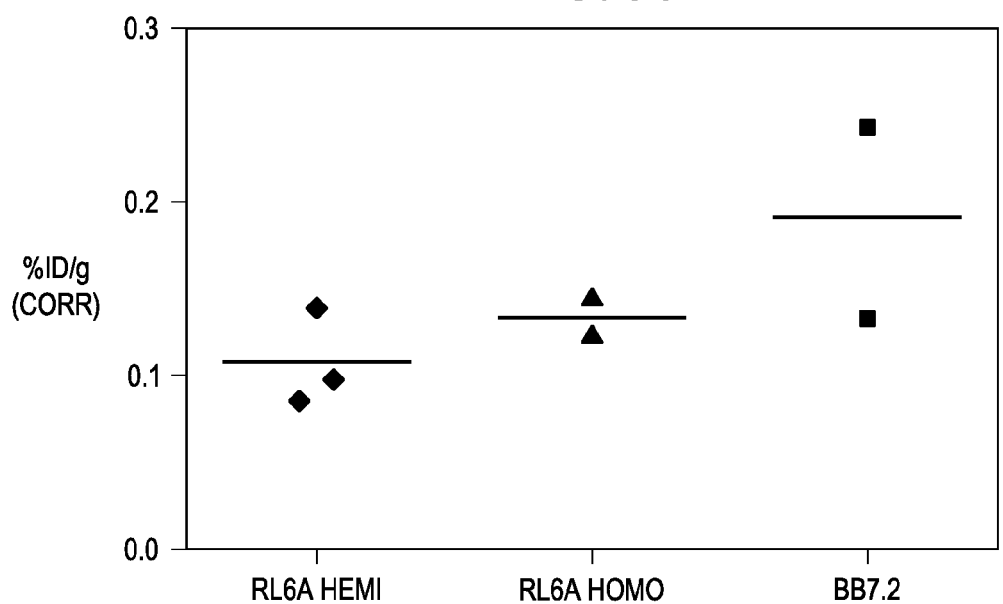
Figure 5D:
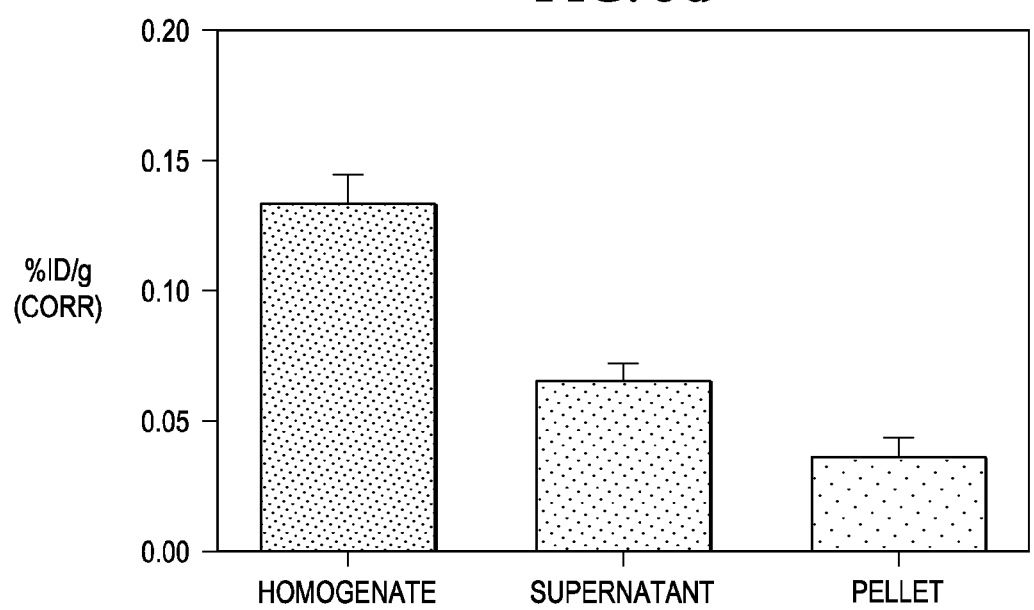
Figure 6A:
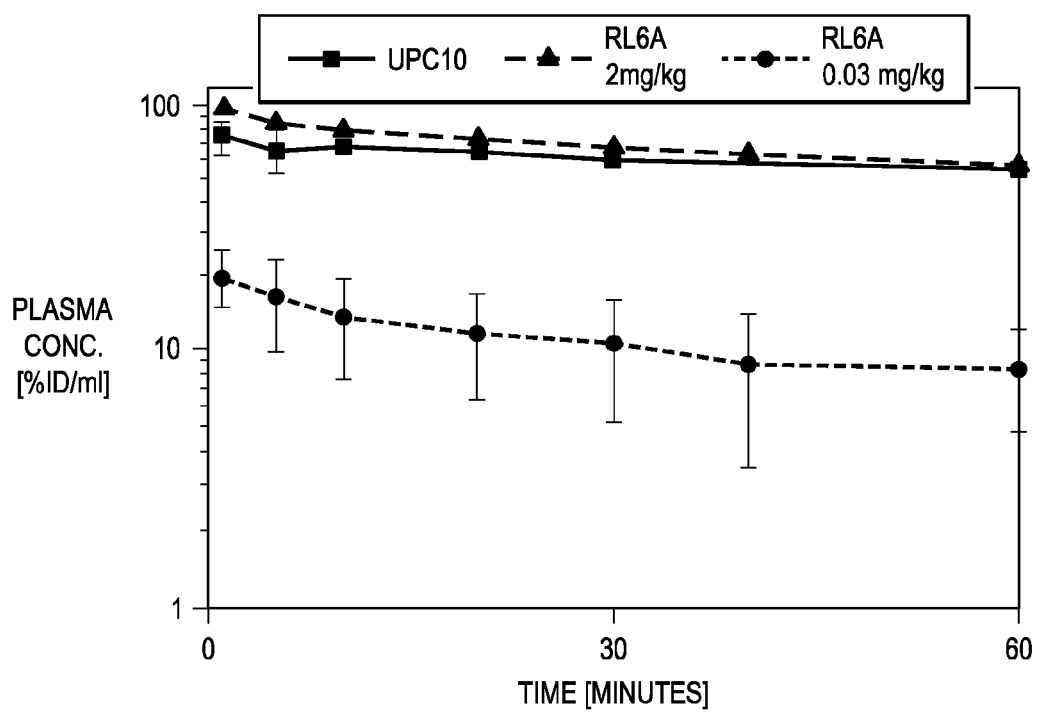
FIG. 6a Plasma kinetics in strain 3475. All mice were treated with IFNγ over 48 h before tracer injection. Mean±SD, n=3-5
Figure 6B:
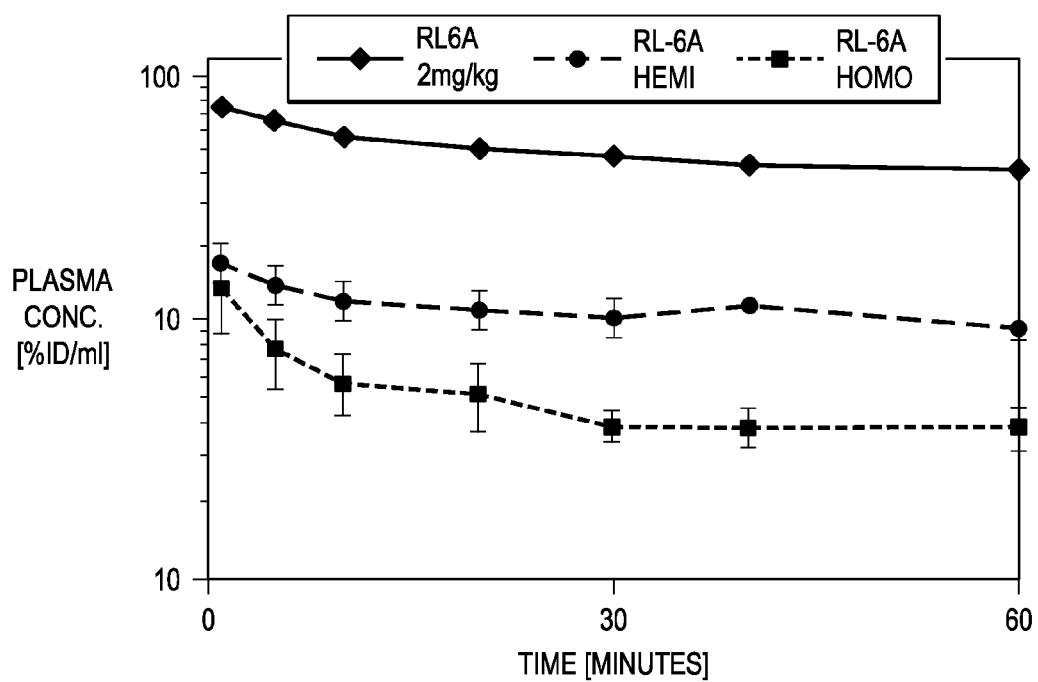
FIG. 6b Plasma kinetics in strain 4191. All mice were treated with I IFNγ over 48 h before tracer injection. Mean±SD, n=2-3

FIGS. 5a-5d show the brain uptake expressed as apparent Vd at 30 μg/kg injected dose (FIG. 5a) and the saturation at 2 mg/kg for both RL-6A and BB7.2. FIG. 5c depicts the brain concentrations after correction for vascular space (8.5 μL/g, value taken from 3475 mice). The RL-6A data are given for hemi and homozygous mice, no statistical comparisons were made at this point due to the small n. FIGS. 6a-6b illustrate the kinetics in plasma obtained in these studies. At the low tracer doses (~30 μg/kg) we observed rapid initial decline of plasma concentrations already at the earliest sampling time compared to UPC10 (FIG. 6a, strain 3475), which indicates clearance from the circulation by binding to peptide-MHC complexes in the body. At the 2 mg/kg dose, plasma pharmacokinetics demonstrates saturation of clearance, with plasma concentration time curves similar to the isotype control antibody. To check for the integrity of the tracers in the in vivo experiments, precipitation by TCA was used. All tracers showed precipitability >98% before injection. Precipitability in plasma samples was typically 98-99% throughout the sampling period and >90% in brain samples.

Making of TCR Mimics.

The heavy and light chains of, e.g., a HLA-A2 Class I molecule are expressed and prepared separately in *E. coli* as insoluble inclusion bodies according to established protocols, solubilized and isolated as tetramers. Balb/c mice (female and male) are immunized with the HLA-A2 tetramers. Each mouse was injected subcutaneously every 2 weeks (up to 5 times) with immunogen (50.mu.g) in PBS which also contained 25 ug of Quil A (adjuvant) in 100 ul. Blood samples from mice were collected into 1.5 ml eppendorf microcentrifuge tubes containing heparin, and plasma was clarified by centrifugation. A significant portion of the antibodies raised against peptide-HLA tetramers are generated against HLA as well as streptavidin (SA) utilized to tetramerize the peptide-HLA complexes; consequently, an assay protocol had to be developed that allowed for detection of a low concentration of specific antibodies in a milieu of non-specific ones. To resolve this problem, a pre-absorption step was incorporated into an ELISA assay format. In the ELISA format, sera from immunized mice are first reacted with HLA-A2 monomers containing another irrelevant peptide before reacting them with HLA-A2 complexes of the relevant peptide. Serum from the immunized mice was used in an ELISA format to identify "peptide-specific" antibody responses. Remember that TCR mimics are antibodies having dual specificity for both peptide and HLA. In addition, the immunized mice will produce antibody specificities against HLA epitopes. It is these antibodies that the pre-absorption protocol substantially removes from the serum samples. In order to substantially remove antibodies that were not peptide specific, a pre-absorption step was included in the protocol.

Using HLA-A2 as an example, a positive control in the assay, BB7.2 mAb was used at 50 to 200 ng/well. This mAb recognizes only conformationally correct forms of the refolded peptide-HLA-A2 molecule. For a negative control in the assay, a peptide-HLA-A2 complex containing an irrelevant peptide was coated on the plate. In this particular assay, the negative control was eIF4G peptide-loaded HLA-A2 monomer.

Hybridomas were generated by submitting 12 mice immunized with 264p-HLA-A2 to the Hybridoma are generated using standard technology. Supernatants are screened for hybridomas to determine if they are producing anti-peptide-HLA specific antibodies. Hybridomas determined positive after a first screening re expanded, and the supernatant are diluted and rescreened by competitive ELISA. Anti-HLA-target plus peptide specificity of TCRm's are validated for generating monoclonal antibodies specific for peptide-HLA complexes.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Bhattacharya R, Xu Y, Rahman M A, Couraud P O, Romero I A, Weksler B B, Weidanz J A, Bickel U. A novel vascular targeting strategy for brain-derived endothelial cells using a TCR mimic antibody. J Cell Physiol 2010; 225: 664-672.

Lee H J, Engelhardt B, Lesley J, Bickel, Pardridge W M. Targeting rat anti-mouse transferrin receptor monoclonal antibodies through blood-brain barrier in mouse. J Pharmacol Exp Ther 2000; 292: 1048-1052.

Neethling F A, Ramakrishna V, Keler T, Buchli R, Woodburn T, Weidanz J A. Assessing vaccine potency using TCR mimic antibodies. Vaccine 2008; 26: 3092-3102.

Verma B, Hawkins O E, Neethling F A, Caseltine S L, Largo S R, Hildebrand W H, Weidanz J A. Direct discovery and validation of a peptide/MHC epitope expressed in primary human breast cancer cells using a TCRm monoclonal antibody with profound antitumor properties. Cancer Immunol Immunother 201 0; 59: 563-573.

Verma B, Neethling F A, Caseltine S, Fabrizio G, Largo S, Duty J A, Tabaczewski P, Weidanz J A. TCR mimic monoclonal antibody targets a specific peptide/HLA class I complex and significantly impedes tumor growth in vivo using breast cancer models. J Immunol 2010; 184: 2156-2165.

Weidanz J A, Nguyen T, Woodburn T, Neethling F A, Chiriva-Internati M, Hildebrand W H, Lustgarten J. Levels of specific peptide-HLA class I complex predicts tumor cell susceptibility to CTL killing. J Immuno/2006; 177: 5088-5097.

Weidanz J A, Piazza P, Hickman-Miller H, Woodburn D, Nguyen T, Wahl A, tŸJeethling F, Chiriva-Internati M, Rinaldo C R, Hildebrand W H. Development and implementation of a direct detection, quantitation and validation system for class I MHC self-peptide epitopes. J Immunol Methods 2007; 318: 47-58.

Weksler B B, Subileau E A, Perriere N, Charneau P, Holloway K, Leveque M, Tricoire-Leignel H, Nicotra A, Bourdoulous S, Turowski P, Male D K, Roux F, Greenwood J, Romero I A, Couraud P O. Blood-brain barrier-specific properties of a human adult brain endothelial cell line. Faseb J 2005; 19: 1872-1874.

What is claimed is:

1. A method of delivering a therapeutic agent into and across an endothelial cell (EC) in a subject in need thereof, comprising:
   attaching to a TCR mimic an active agent to form a therapeutic agent, wherein the TCR mimic is capable of binding a human HLA-A2 cell surface protein and crossing a brain EC microvascular barrier into the brain; and
   administering to the subject the therapeutic agent in a pharmaceutically acceptable carrier, wherein the therapeutic agent effectively crosses the brain EC microvascular barrier into the brain.

2. The method of claim 1, wherein the barrier being crossed is the blood-brain barrier (BBB), in a subject with (i) a CNS disease or disorder or (ii) a peripheral disease or disorder with CNS involvement.

3. The method of claim 2, wherein the disease or disorder is a brain tumor.

4. The method of claim 1, wherein the therapeutic agent or carrier is directly conjugated to a targeting molecule by covalent bonding which conjugation is optionally effected via a spacer or linker that bridges between the therapeutic agent or carrier and the targeting molecule.

5. The method of claim 4, wherein the therapeutic agent-targeting molecule conjugate or carrier-targeting molecule conjugate is a recombinant fusion polypeptide.

6. The method of claim 1, wherein the active agent is an antineoplastic agent.

7. The method of claim 1, wherein the subject has or is suspected of a metabolic disorder.

8. A method for treating a neuronal disease or condition comprising:
   identifying a subject in need of such treatment for the neuronal disease or condition;
   administering to the subject in need of such treatment a neuroprotective and/or neurorestorative agent in an amount effective to treat the disorder in the subject, wherein the agent comprises:
   a TCR mimic that targets an MHC-peptide combination, wherein the MHC is a human HLA-A2 protein found on the surface of an endothelial cells of the neuronal vasculature that is conjugated to an active agent to form a therapeutic agent, wherein the TCR mimic is capable of crossing a brain EC microvascular barrier into the brain.

9. The method of claim 8, wherein the disease or disorder is a brain tumor.

10. The method of claim 8, wherein the therapeutic agent or carrier is directly conjugated to a targeting molecule by covalent bonding; which conjugation is optionally effected via a spacer or linker that bridges between the therapeutic agent or carrier and the targeting molecule.

11. The method of claim 10, wherein the therapeutic agent-targeting molecule conjugate or carrier-targeting molecule conjugate is a recombinant fusion polypeptide.

12. The method of claim 8, wherein the step of administering intravenously.

13. The method of claim 8, wherein the subject has or is suspected of having a metabolic disorder.

14. The method of claim 8, wherein the active agent is an antineoplastic agent.

15. A method for treating a disease or condition in which a therapeutic agent has to cross an epithelial layer of a vasculature comprising:
    identifying a subject in need of such treatment for the disease or condition;
    administering to the subject in need of such treatment the therapeutic agent in an amount effective to treat the disorder in the subject, wherein the agent comprises:
    a TCR mimic that targets an MHC-peptide combination, wherein the MHC is a human HLA-A2 protein found on the surface of an endothelial cells that is conjugated to an active agent to form a therapeutic agent, wherein the TCR mimic is selected to cross a brain EC microvascular barrier into the brain.

16. The method of claim 15, wherein the active agent is an antineoplastic agent.

17. The method of claim 15, wherein the TCR mimic is RL6.

18. A method of delivering a therapeutic agent into and across an endothelial cell (EC) in a subject in need thereof, comprising:
    attaching to a TCR mimic an active agent to form a therapeutic agent, wherein the TCR mimic is RL6, wherein the TCRm and is capable of crossing a brain EC microvascular barrier into the brain; and
    administering to the subject the therapeutic agent in a pharmaceutically acceptable carrier, wherein the therapeutic agent effectively crosses the brain EC microvascular barrier into the brain.

19. The method of claim 18, wherein the barrier being crossed is the blood-brain barrier (BBB), in a subject with (i) a CNS disease or disorder or (ii) a peripheral disease or disorder with CNS involvement.

20. The method of claim 18, wherein the therapeutic agent or carrier is directly conjugated to a targeting molecule by covalent bonding which conjugation is optionally effected via a spacer or linker that bridges between the therapeutic agent or carrier and the targeting molecule.

21. The method of claim 18, wherein the active agent is an antineoplastic agent.

* * * * *

UNITED STATES PATENT AND TRADEMARK OFFICE
CERTIFICATE OF CORRECTION

PATENT NO.         : 9,555,108 B2
APPLICATION NO.    : 14/007164
DATED              : January 31, 2017
INVENTOR(S)        : John A. Weidanz and Ulrich Bickel Page 1 of 1

It is certified that error appears in the above-identified patent and that said Letters Patent is hereby corrected as shown below:

In the Specification

Column 1, Line 13, please add the following paragraph:
STATEMENT OF FEDERALLY FUNDED RESEARCH
"This invention was made with government support under W81XWH-12-1-0184 awarded by the US Army Medical Research Acquisition Act. The government has certain rights in the invention."

Signed and Sealed this
Twenty-fourth Day of September, 2019

Andrei Iancu
*Director of the United States Patent and Trademark Office*